(12) United States Patent
Sachse et al.

(10) Patent No.: US 11,602,270 B2
(45) Date of Patent: Mar. 14, 2023

(54) DEVICES AND METHODS FOR MAPPING CARDIAC TISSUE

(71) Applicant: University of Utah Research Foundation, Salt Lake City, UT (US)

(72) Inventors: Frank B. Sachse, Salt Lake City, UT (US); Robert W. Hitchcock, Salt Lake City, UT (US); Nassir F. Marrouche, Park City, UT (US); Nathan J. Knighton, Salt Lake City, UT (US); Chao Huang, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 167 days.

(21) Appl. No.: 16/482,389

(22) PCT Filed: Jan. 31, 2018

(86) PCT No.: PCT/US2018/016314
§ 371 (c)(1),
(2) Date: Jul. 31, 2019

(87) PCT Pub. No.: WO2018/144648
PCT Pub. Date: Aug. 9, 2018

(65) Prior Publication Data
US 2020/0022573 A1    Jan. 23, 2020

Related U.S. Application Data

(60) Provisional application No. 62/453,025, filed on Feb. 1, 2017.

(51) Int. Cl.
*A61B 1/313*         (2006.01)
*G16H 30/40*         (2018.01)
(Continued)

(52) U.S. Cl.
CPC ........ *A61B 1/3137* (2013.01); *A61B 1/00194* (2022.02); *A61B 1/05* (2013.01);
(Continued)

(58) Field of Classification Search
CPC ................ A61B 18/06; A61B 18/1492; A61B 1/00009; A61B 1/05; A61B 1/3137;
(Continued)

(56) References Cited

U.S. PATENT DOCUMENTS 5,429,131 A    7/1995   Scheinman et al.
5,687,737 A    11/1997  Branham et al.
(Continued)

FOREIGN PATENT DOCUMENTS

CN    101453942 A    6/2009
CN    103747756 A    4/2014
(Continued)

OTHER PUBLICATIONS

U.S. Appl. No. 15/222,858, dated Jan. 23, 2020, Office Action.
(Continued)

*Primary Examiner* — Jonathan T Kuo
(74) *Attorney, Agent, or Firm* — Workman Nydegger

(57) ABSTRACT

The present disclosure relates to systems and methods for generating three-dimensional tissue maps, and particularly fibrosis maps of cardiac tissue. An intravascular device includes an elongated member and a distal tip. An imaging assembly is integrated with the elongated member to enable imaging of the microstructure of tissue near the distal tip. One or more navigation electrodes are positioned at or near the distal tip. Electrical mapping and/or ablation assemblies may also be integrated with the device. Images may be characterized according to a level of fibrosis and, using the corresponding determined locations of the images, a three-dimensional map showing areas of differential fibrosis may (Continued)

be generated. Electrical mapping data may also be integrated with the fibrosis map to generate a composite fibrosis and voltage map.

21 Claims, 14 Drawing Sheets

(51) Int. Cl.
```
    G16H 40/63      (2018.01)
    A61B 1/05       (2006.01)
    A61B 5/0205     (2006.01)
    A61B 5/06       (2006.01)
    A61B 5/00       (2006.01)
    A61B 18/06      (2006.01)
    A61B 18/14      (2006.01)
    A61B 5/287      (2021.01)
    A61B 1/00       (2006.01)
    A61B 18/00      (2006.01)
    A61B 18/02      (2006.01)
```
(52) U.S. Cl.
CPC .......... *A61B 5/02055* (2013.01); *A61B 5/068* (2013.01); *A61B 5/287* (2021.01); *A61B 5/4839* (2013.01); *A61B 18/06* (2013.01); *A61B 18/1492* (2013.01); *G16H 30/40* (2018.01); *G16H 40/63* (2018.01); *A61B 2018/00357* (2013.01); *A61B 2018/00577* (2013.01); *A61B 2018/00839* (2013.01); *A61B 2018/0212* (2013.01)

(58) Field of Classification Search
CPC ........... A61B 2018/00357; A61B 2018/00577; A61B 2018/00815; A61B 2018/00821; A61B 2018/00839; A61B 2018/0212; A61B 2090/064; A61B 5/01; A61B 5/02055; A61B 5/0538; A61B 5/068; A61B 5/14539; A61B 5/14542; A61B 5/287; A61B 5/4839; A61B 5/6852; G16H 30/40; G16H 40/63; G16H 50/00–50/80

See application file for complete search history.

(56) References Cited

U.S. PATENT DOCUMENTS

| | | | |
|---|---|---|---|
| 6,004,269 A | 12/1999 | Crowley et al. | |
| 6,228,082 B1 | 5/2001 | Baker et al. | |
| 7,001,383 B2* | 2/2006 | Keidar | A61B 18/1492 606/41 |
| 7,499,153 B2 | 3/2009 | Puppels et al. | |
| 8,029,766 B2* | 10/2011 | Elmaleh | A61B 5/0084 424/9.6 |
| 8,059,274 B2* | 11/2011 | Splinter | A61B 5/6852 356/364 |
| 8,106,905 B2 | 1/2012 | Markowitz | |
| 8,316,861 B2 | 11/2012 | Brewer et al. | |
| 8,432,542 B2 | 4/2013 | Marple et al. | |
| 8,496,579 B2 | 7/2013 | Koenig et al. | |
| 8,876,815 B2 | 11/2014 | Coe et al. | |
| 9,763,642 B2 | 9/2017 | Harks et al. | |
| 10,143,398 B2* | 12/2018 | Altmann | A61B 8/12 |
| 10,231,706 B2* | 3/2019 | Chen | A61B 8/12 |
| 2004/0054366 A1 | 3/2004 | Davison | |
| 2004/0092806 A1 | 5/2004 | Sagon et al. | |
| 2004/0092846 A1 | 5/2004 | Sagon et al. | |
| 2004/0153057 A1 | 8/2004 | Davison | |
| 2004/0254474 A1 | 12/2004 | Seibel et al. | |
| 2005/0033135 A1 | 2/2005 | Govari | |
| 2005/0148836 A1 | 7/2005 | Kleen et al. | |
| 2005/0242298 A1 | 11/2005 | Genet | |
| 2005/0288665 A1 | 12/2005 | Woloszko | |
| 2006/0041199 A1* | 2/2006 | Elmaleh | A61B 5/02007 600/478 |
| 2006/0229515 A1 | 10/2006 | Sharareh et al. | |
| 2006/0253031 A1* | 11/2006 | Altmann | A61B 8/0883 600/466 |
| 2007/0038123 A1 | 2/2007 | Fulghum | |
| 2007/0179397 A1 | 8/2007 | Hashimshony et al. | |
| 2007/0299352 A1 | 12/2007 | Harlev et al. | |
| 2007/0299353 A1 | 12/2007 | Harlev et al. | |
| 2008/0183036 A1 | 7/2008 | Saadat et al. | |
| 2008/0262359 A1 | 10/2008 | Tearney et al. | |
| 2008/0306391 A1 | 12/2008 | Hular et al. | |
| 2009/0076375 A1* | 3/2009 | Maschke | A61B 34/73 600/411 |
| 2009/0076498 A1 | 3/2009 | Saadat | |
| 2009/0147257 A1* | 6/2009 | Splinter | A61B 5/6852 356/364 |
| 2009/0231578 A1 | 9/2009 | Ling et al. | |
| 2009/0299195 A1 | 12/2009 | Muller et al. | |
| 2009/0326320 A1 | 12/2009 | Sinofsky et al. | |
| 2011/0028967 A1 | 2/2011 | Rollins et al. | |
| 2011/0082451 A1 | 4/2011 | Melsky | |
| 2011/0118590 A1 | 5/2011 | Zhang | |
| 2011/0301438 A1 | 12/2011 | Sachse et al. | |
| 2012/0053452 A1 | 3/2012 | Roy | |
| 2012/0075619 A1 | 3/2012 | Nieman et al. | |
| 2012/0108957 A1 | 5/2012 | Desai | |
| 2012/0172724 A1 | 7/2012 | Hill et al. | |
| 2012/0281218 A1 | 11/2012 | Schnitzer et al. | |
| 2012/0302892 A1 | 11/2012 | Lue et al. | |
| 2013/0102862 A1 | 4/2013 | Mercader et al. | |
| 2013/0218019 A1 | 8/2013 | Abraham | |
| 2013/0315455 A1 | 11/2013 | Wakai | |
| 2014/0018792 A1 | 1/2014 | Gang | |
| 2014/0031802 A1 | 1/2014 | Melsky et al. | |
| 2014/0058246 A1 | 2/2014 | Boveja et al. | |
| 2014/0081113 A1 | 3/2014 | Cohen et al. | |
| 2014/0088418 A1 | 3/2014 | Radulescu et al. | |
| 2014/0171942 A1 | 6/2014 | Werneth et al. | |
| 2015/0011843 A1 | 1/2015 | Toth et al. | |
| 2015/0119708 A1 | 4/2015 | Sachse et al. | |
| 2015/0182282 A1 | 7/2015 | Zemel | |
| 2015/0351722 A1* | 12/2015 | Chen | A61B 8/445 600/427 |
| 2016/0228180 A1 | 8/2016 | Sliwa et al. | |
| 2017/0027503 A1 | 2/2017 | Sachse et al. | |
| 2017/0061617 A1 | 3/2017 | Cochet et al. | |
| 2018/0103852 A1 | 4/2018 | Dagdeviren et al. | |
| 2019/0223706 A1 | 7/2019 | Takeuchi et al. | |

FOREIGN PATENT DOCUMENTS

| | | |
|---|---|---|
| CN | 105163651 A | 12/2015 |
| EP | 2712546 A1 | 4/2014 |
| JP | 2004-160212 A | 6/2004 |
| JP | 2005-152654 A | 6/2005 |
| JP | 2008-504557 A | 2/2008 |
| JP | 2009-539566 A | 11/2009 |
| JP | 2012-196437 A | 10/2012 |
| JP | 2016-536065 A | 11/2016 |
| WO | 2006020920 | 2/2006 |
| WO | 2006020920 A2 | 2/2006 |
| WO | 2007146864 | 12/2007 |
| WO | 2007146864 A2 | 12/2007 |
| WO | 2014028584 | 2/2014 |
| WO | 2014028584 A2 | 2/2014 |
| WO | 2014165990 | 10/2014 |
| WO | 2014165990 A2 | 10/2014 |
| WO | 2015073932 | 5/2015 |
| WO | 2015/165978 A1 | 11/2015 |
| WO | 2016/181318 A1 | 11/2016 |
| WO | 2016/205731 A1 | 12/2016 |
| WO | 2018/144648 A1 | 8/2018 |

OTHER PUBLICATIONS

International Search Report and Written Opinion issued in PCT/US2018/016314 dated Mar. 2, 2018.

(56) References Cited

OTHER PUBLICATIONS

International Search Report and Written Opinion for PCT/US2016/044845 dated Oct. 7, 2016.
International Search Report and Written Opinion for PCT/US2018/016314 dated Mar. 28, 2018.
U.S. Appl. No. 15/222,858, dated Feb. 28, 2019, Office Action.
U.S. Appl. No. 15/222,858, dated Nov. 15, 2019, Final Office Action.
Diaz et al., "Spectral classifier design with ensemble classifiers and misclassification-rejection: application to elastic-scattering spectroscopy for detection of colonic neoplasia", Journal of biomedical optics., 16.6 (2011), 067009.
Femnou et al., "Intra cardiac Side-Firing Light Catheter for Monitoring Cellular Metabolism using Transmural Absorbance Spectroscopy of Perfused Mammalian Hearts", JoVE (Journal of Visualized Experiments), 147 (2019):e58992.
Final Office Action received for U.S. Appl. No. 15/222,858, dated Aug. 11, 2020, 13 pages.
Knighton et al., "Towards Cardiac Tissue Characterization Using Machine Learning and Light-Scattering Spectroscopy," USA, 84112, 2015, 26 pages.
Knighton et al., "Towards Intraoperative Quantification of Atrial Fibrosis Using Light Scattering Spectroscopy and Convolutional Neural Networks," UT 84112, USA, 16 pages.
Non-Final Office Action received for U.S. Appl. No. 15/222,858, dated Jan. 4, 2021, 13 pages.
Rajitha et al., "Machine learning classification of human joint tissue from diffuse reflectance spectroscopy data", Biomedical optics express, 10.8 (2019): 3889-3898.
International Search Report and Written Opinion received for PCT Patent Application No. PCT/US2020/065648, dated May 7, 2021, 12 pages.

* cited by examiner

Locate Tissue Regions

Normal Tissue    Image/Measure Fibrosis    Fibrotic Tissue

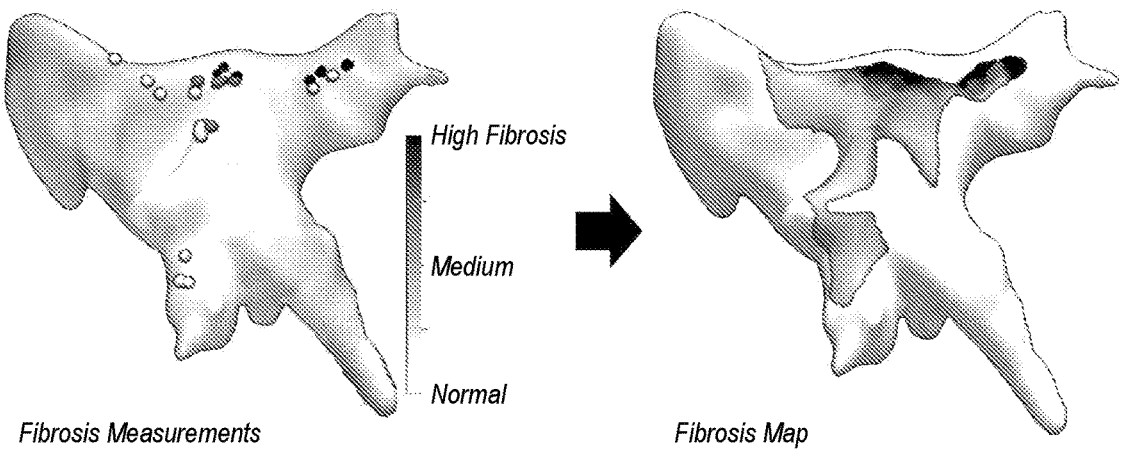
FIG. 14A  FIG. 14B
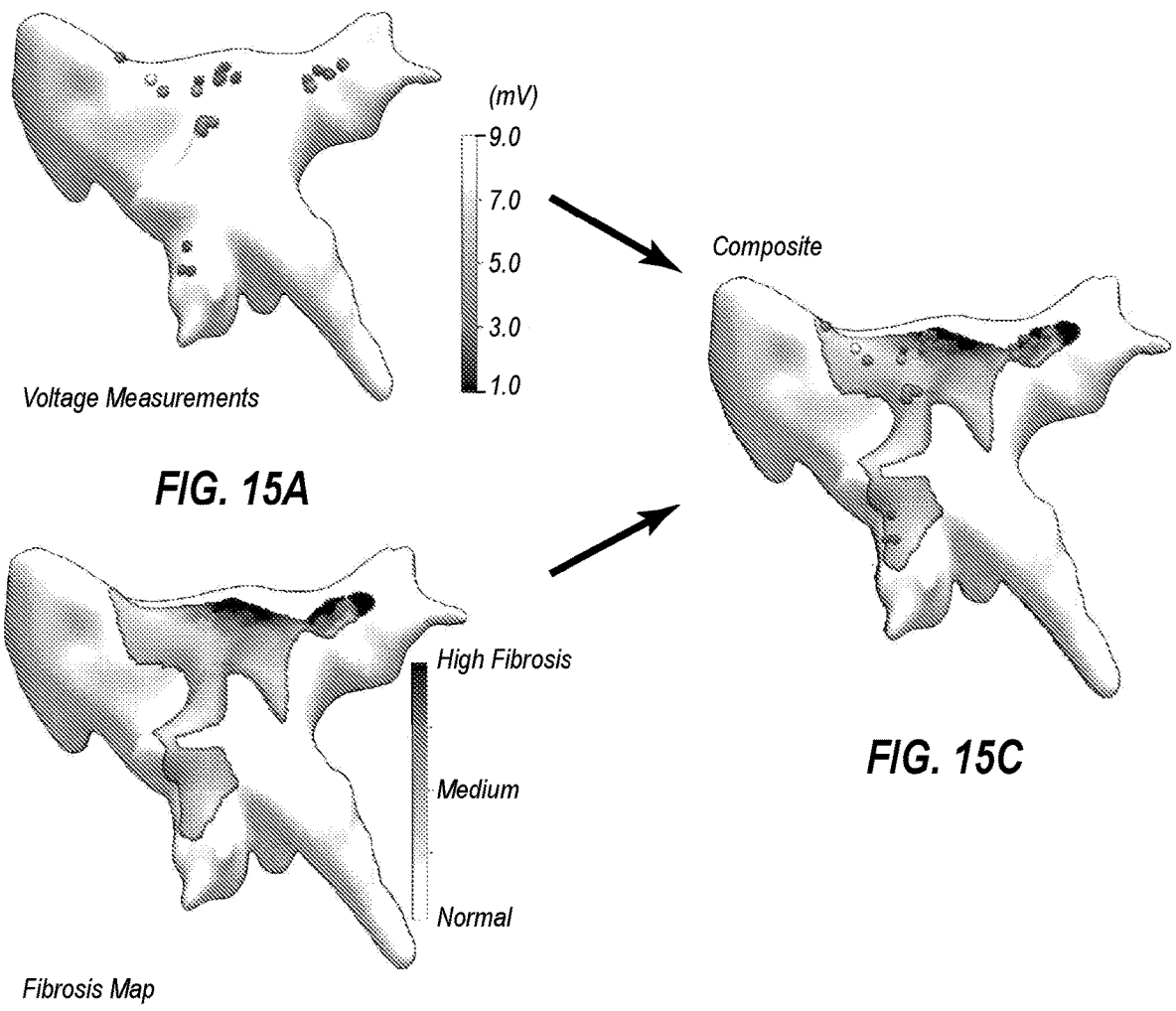
FIG. 15A
FIG. 15B
FIG. 15C

Fibrosis Measurements

Voltage Map

Composite

DEVICES AND METHODS FOR MAPPING CARDIAC TISSUE

CROSS-REFERENCE TO RELATED APPLICATIONS

This application is a U.S. National Stage Application of PCT/US2018/016314 filed Jan. 31, 2018 and titled "Devices and Methods for Mapping Cardiac Tissue", which claims the benefit of and priority to U.S. Provisional Patent Application Ser. No. 62/453,025, filed Feb. 1, 2017 and titled "Methods for Catheterized Microscopic Imaging and Electrical mapping of Cardiac Tissue," the entireties of which are incorporated herein by this reference.

BACKGROUND

Atrial fibrillation ("AF") is the most common type of sustained cardiac arrhythmia and causes significant disease burden in our society. Typical AF treatment involves rate control using drugs, such as beta blockers, and anticoagulation to prevent thromboembolism. However, for patients who remain symptomatic, rhythm control with antiarrhythmic medications and/or transcatheter ablation are commonly chosen treatment options. Catheter ablation involves selectively destroying tissue regions, a process usually achieved by applying radio frequency ("RF") energy to heat the tissue. Several trials have suggested that catheter ablation can lead to maintained long-term sinus rhythm in AF patients. Nevertheless, the recurrence rate of AF after ablation is as high as 50%. Additionally, 20-40% of AF patients will undergo multiple ablation procedures.

In part, these complications are explained by the complexity of ablation procedures, which are conventionally performed remotely and without direct visualization of the treated tissue. One advance that has been promoted to reduce procedural complexity and assess outcomes of procedures is based on endocardial voltage mapping. While voltage mapping is helpful in assessing acute changes to electrical conduction in tissue at centimeter scale, it cannot provide reliable information as to whether a particular ablation produced a sustainable scar and persistently blocks electrical conduction. Despite previous technological advances, long-term maintenance of sinus rhythm in AF patients after ablation remains elusive.

An increased AF risk is associated with remodeling of the atrial tissue in the form of fibrosis, which occurs as a maladaptive response to metabolic, hemodynamic, and ischemic stresses. Fibrosis is defined as the excessive formation of connective tissue comprising, in particular, extracellular matrix, fibroblasts and myofibroblasts. During episodes of AF, extracellular matrix proteins including collagen-1 and fibronectin-1 are excessively produced and released into atrial tissues. Fibrosis significantly alters the mechanical properties of cardiac tissues. One effect is that fibrosis reduces atrial mechanical function as quantified, e.g., by atrial strain.

Macroscopic regions of atrial fibrosis can be visualized using magnetic resonance imaging (MRI), for instance, late gadolinium enhanced MRI. However, not all care centers have access to the requisite and relatively expensive MRI equipment, and such procedures are associated with high costs. Further, while MRI imaging may detect fibrosis at the macroscopic scale, it does not provide insights into the microscopic distribution and composition of fibrosis.

An established clinical tool for assessment of ventricular tissue microstructure and fibrosis is endomyocardial biopsy, which requires an invasive procedure for tissue extraction. Further, the procedure is only rarely performed in the atria due to its high complication rate.

Accordingly, there exists a long felt and ongoing need for devices and methods capable of imaging cardiac tissue at the microstructure scale. Also needed are devices and methods for providing ablation of targeted cardiac tissue and assessing the effects of ablation during the ablation procedure. Such advances will beneficially improve outcomes and reduce disease burden.

BRIEF SUMMARY

The present disclosure relates to devices, systems, and methods for in-situ imaging, at a microstructural level, of tissue within a patient's body. In one embodiment, an intravascular device includes an elongated member with a proximal end and a distal end. A distal tip is disposed at or near the distal end. The intravascular device is configured such that the distal tip may be delivered to targeted tissue (e.g., cardiac tissue) within the patient's body. The intravascular device includes an imaging assembly. The imaging assembly includes an optical housing disposed at the distal tip which is configured to house one or more imaging components to enable imaging of tissue at or near the distal tip. The intravascular device also includes a localization assembly. The localization assembly includes one or more localization components disposed at or near the distal tip, and the localization assembly is configured to provide location information of the distal tip within the three-dimensional anatomical working space.

In some embodiments, the localization assembly includes one or more localization electrodes disposed at the distal tip. The one or more localization electrodes may be communicatively coupled to a reference electrode to enable the generation of localization data relative to the reference electrode.

In some embodiments, the intravascular device further includes a treatment assembly having one or more treatment components disposed at the distal tip for treating targeted tissue. The treatment assembly may include, for example, one or more energy transmission components that enable the transmission of energy to the distal tip. The energy transmitted to the distal tip may be used to ablate targeted tissue at or near the distal tip. Some embodiments include an energy transmission member that extends through the elongated member and is operatively coupled to the distal tip. The energy transmission member may be configured, for example, to transmit RF energy to the distal tip. Other treatment assemblies may additionally or alternatively be configured for delivering one or more of a treatment chemical (e.g., alcohol), cryotherapeutic agent, or drug.

In preferred embodiments, the imaging assembly is configured to provide imaging of targeted tissue at a subcellular and/or submicron resolution. In some embodiments, the imaging assembly is arranged as a fiber-optic confocal microscope (FCM) system (e.g., capable of providing imaging of targeted tissue at a depth of at least about 5 µm.

In certain embodiments, the intravascular device further includes an electrical assembly configured for measuring one or more electrical readings (e.g., voltage) at targeted tissue. The electrical assembly may include one or more electical sensors disposed at the distal tip. For example, at least a portion of the distal tip may be configured as an electrode, and the electrode may be operatively coupled to an electrically conductive member that extends through the elongated member to the distal tip.

In some embodiments, the distal tip includes separate sections electrically insulated from one another. For example, a first section may be operatively coupled to the treatment assembly and be configured to operate as an ablation electrode capable of transmitting energy to targeted tissue, and a second section may be operatively coupled to the electrical assembly and be configured to operate as an electrical electrode capable of measuring voltages at targeted tissue.

Intravascular devices described herein may also be included as part of a system configured for generating a three-dimensional map of one or more tissue microstructure attributes. In one embodiment, such a system includes an intravascular device as described herein and a computer system configured to: receive a plurality of tissue microstructure images obtained by the intravascular device; determine a location within the three-dimensional anatomical working space for each of the tissue microstructure images to obtain a plurality of image locations; characterize each of the tissue microstructure images according to an exhibited level of a tissue microstructure attribute; and based on the characterized images, and based on the corresponding image locations, generate a three-dimensional tissue microstructure attribute map of the anatomical working space.

Each tissue microstructure image may be characterized according to an exhibited level of a tissue microstructure attribute (e.g., fibrosis) by determining one or more of image spatial regularity, average pixel intensity, and area fraction of bright regions, where bright regions are determined according to a brightness threshold.

In some embodiments, the computer system is further configured to: receive a plurality of tissue electrical readings obtained by the intravascular device; determine a location within the three-dimensional anatomical working space for each of the tissue electrical readings to obtain a plurality of electrical reading locations; and based on the electrical readings and their corresponding locations, generate a three-dimensional electrical map of the anatomical working space associating the plurality of tissue electrical readings with their corresponding locations within the anatomical working space. The tissue microstructure attribute map and the electrical map may be combined into a composite map.

In some embodiments, the system further includes a user interface device, and the computer system is configured to render the three-dimensional attribute map and/or composite map on the user interface device.

In one embodiment, a method of generating a three-dimensional tissue attribute map includes the steps of: providing an intravascular device such as described herein; directing the distal tip of the intravascular device to a plurality of tissue locations (e.g., a plurality of locations within the heart); at each location, operating the intravascular device to obtain one or more tissue microstructure images; at each location, operating the intravascular device to determine the location of the distal tip within the three-dimensional anatomical working space; associating each tissue microstructure image with its corresponding determined location within the anatomical working space; characterizing each tissue microstructure image according to a level of an exhibited attribute (e.g., fibrosis); and based on the characterized images and their corresponding locations, generating a three-dimensional map (e.g., fibrosis map) of the anatomical working space. In certain implementations, the method may be performed in a blood-filled, beating heart in-situ.

The method may further include the steps of: at each location, operating the intravascular device to obtain one or more electrical readings; associating each electrical reading with its corresponding determined location within the anatomical working space; based on the obtained electrical readings and their corresponding locations, generating a three-dimensional electrical map of the anatomical working space; and combining the electrical map and the microstructure attribute map (e.g., fibrosis map) to generate a composite map.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 14A and 14B illustrate an interpolation process for generating a "heat-map" style rendering from a point map rendering;

FIGS. 15A through 16C illustrate various composite maps combining both fibrosis maps and voltage maps.

DETAILED DESCRIPTION

Introduction

Figure 1:
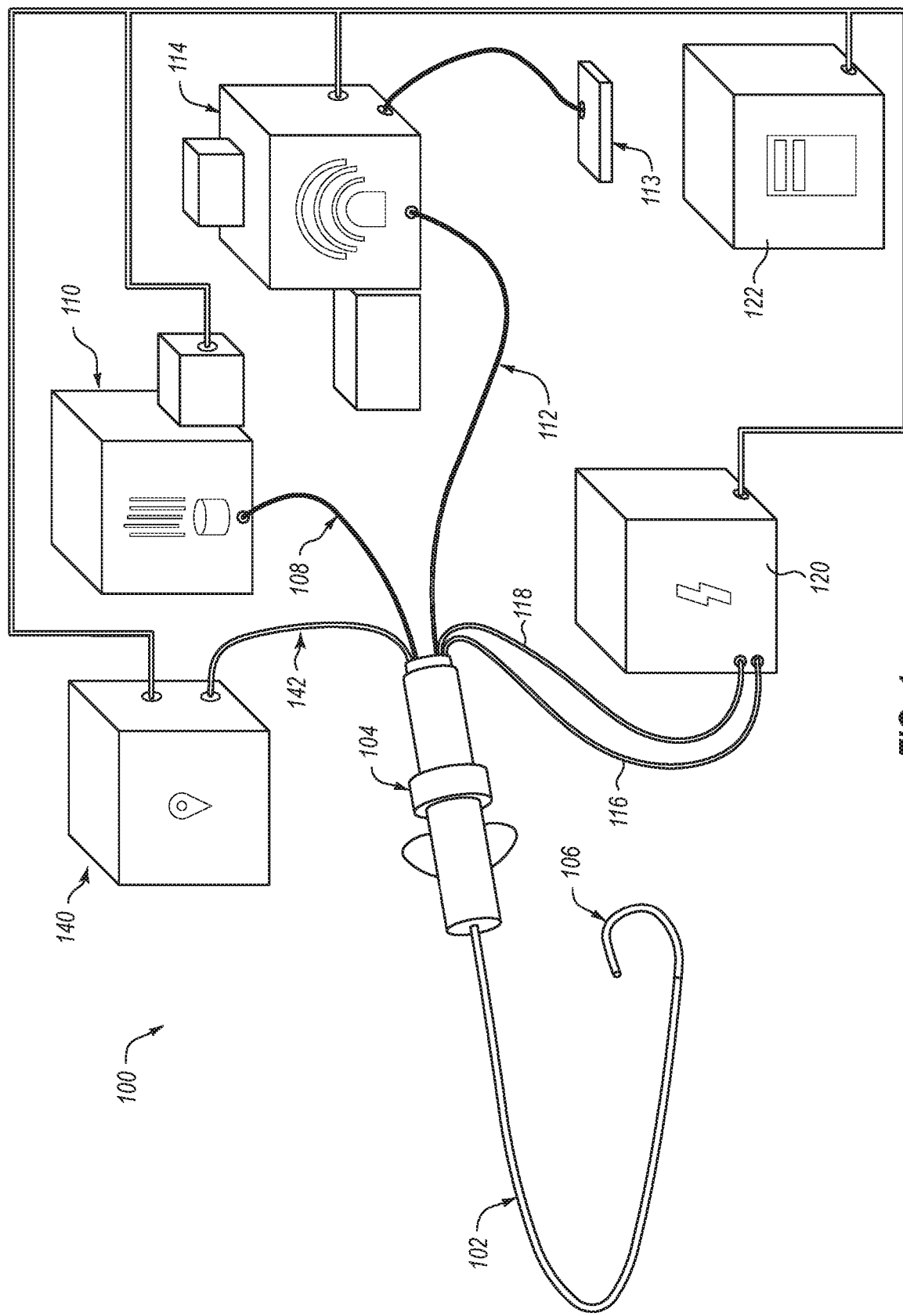
FIG. 1 illustrates an overview of an exemplary system for obtaining tissue microstructure images and corresponding locations, and for generating a three-dimensional map of the imaged anatomy.

The present disclosure relates to devices and methods for visualizing cardiac tissue at the microstructure level. Certain embodiments are configured for providing real-time imaging of targeted cardiac tissue microstructure. Embodiments described herein include intravascular devices (e.g., catheters) configured for providing imaging and localization data. For example, such an intravascular device may include an imaging assembly and a localization assembly. The imaging assembly includes features enabling the device to obtain images of cardiac tissue microstructure, and the localization assembly includes features for determining a corresponding location within the targeted anatomy.

In use, gathered image and location data may be combined to generate a three-dimensional fibrosis map of a targeted heart chamber. For example, the distal tip of the device may be routed to the targeted heart chamber, where a plurality of images are obtained (using the imaging assembly) at a plurality of locations (determined using the localization assembly). Each image may be characterized according to the degree of fibrosis shown. A three-dimensional fibrosis map of the heart chamber may then be generated based on the characterized images and their corresponding image locations. The fibrosis map may greatly aid practitioners in diagnosing fibrosis, targeting fibrosis for treatment, providing treatment options, and monitoring treatment.

Certain embodiments described herein are configured for visualizing targeted tissue at the microstructural level. As used in this disclosure, this level of imaging includes visualization of targeted tissue at the cellular and tissue microstructural level, such as at a subcellular resolution capable of showing tissue and cellular-level detail (e.g., a submicron resolution). For example, certain devices described herein are capable of visualizing microstructural abnormalities and/or cellular-level treatment response. Although preferred embodiments are configured for such a high-level resolution, other embodiments need not necessarily provide resolution at such detail. For example, some embodiments may be limited to a sub-millimeter resolution and/or a resolution that is greater than that of a typical MRI process but less than the preferred subcellular resolution.

Throughout this disclosure, particular examples are provided in the context of imaging, treating, and/or mapping cardiac tissue within the left atrium, it will be understood that the described components and features may also be utilized in other targeted heart chambers or even in other anatomical locations outside of the heart. For example, other internal tissues which may be targeted using embodiments described herein include pulmonary, gastrointestinal, urogynecologic, endocrine, neural, and vascular tissues. The anatomical region where targeted tissues are located is referred to herein as the "anatomical working space." Although certain embodiments are beneficially capable of providing imaging, treating, and/or mapping within a blood-filled, beating heart, not all embodiments are necessarily limited to an implementation where the heart is in this state. For example, features and embodiments described herein may be utilized in situations where a heart is on bypass or is otherwise arrested.

When describing features relating to imaging, many of the examples below utilize confocal microscopy. It will be understood, however, that other imaging methods may additionally or alternatively be utilized. For example, some embodiments be configured for, in addition to or as an alternative to confocal microscopy, fluorescence microscopy, multiphoton imaging, optical coherence tomography, hyperspectral imaging, other subcellular resolution optical imaging systems, and combinations thereof. Imaging assembly components may thus be substituted or adjusted as necessary to enable desired imaging modalities.

Moreover, certain embodiments described herein include a treatment assembly configured for treating targeted cardiac tissue. In many examples, the treatment assembly is illustrated and described as an ablation assembly. Typically, ablation components utilize RF energy to generate heat sufficient to kill targeted cells and tissues. It will be understood, however, that other treatment methods may additionally or alternatively be utilized. For example, in some embodiments the treatment assembly may be configured to apply direct heat or other forms of energy, a cryotherapeutic agent, alcohol, other cell killing agents, or combinations thereof. Some embodiments may additionally or alternatively be configured to deliver one or more beneficial treatment agents/drugs, such as cytotoxins, antifibrotic drugs, anti-inflammatory drugs, ion channels blockers and activators, cytokines, other drugs, or combinations thereof.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Moreover, the term "at," when used in the context of a positional relationship, represents a relationship that is directly coincident or a relationship where two or more components are "near" each other. For example, unless specified otherwise, where a component is described as being "at" a distal tip, it will be understood that the component need not be exactly coincident with the very distal end of the tip, but may be near the distal tip (e.g., within about 1 to 3 cm or otherwise close enough to provide its intended function).

System Overview

FIG. 1 illustrates an exemplary intravascular system 100 configured for mapping a heart chamber according to visualized cardiac tissue microstructure. Certain embodiments of the intravascular system 100 may also be configured to treat targeted cardiac tissue and/or determine and map tissue electrical activity (e.g., voltage levels). The illustrated embodiment includes an elongated member 102 (e.g., catheter) with a proximal end coupled to a control handle 104 and a distal tip 106. The elongated member 102 may include a steerable sheath operated by adjusting tension in one or more control wires or by using other steerable catheter components known in the art.

The illustrated system 100 includes an imaging assembly comprising an imaging module 110, one or more imaging components (described in greater detail below) disposed at the distal tip 106, and an optical transmission member 108 extending to the distal tip 106 and operatively coupling to the one or more imaging components. The imaging module 110 may include one or more light source components and one or more light detector components. For example, the imaging module 110 may be configured for selective generation of light at a desired wavelength for transmission through the optical transmission member 108 toward the distal tip 106. The optical transmission member 108 extends through the elongated member 102 to the distal tip 106. In some embodiments, the optical transmission member 108 is a fiber optic bundle capable of transmitting light from the imaging module 110 toward the distal tip 106 and/or transmitting light from the distal tip 106 to the imaging module 110. In some embodiments, the imaging assembly is configured as a fiber-optic confocal microscope (FCM) system.

The illustrated system 100 also includes a treatment assembly. In this particular embodiment, the treatment assembly comprises an ablation treatment module 114, one or more treatment components disposed at the distal tip 106, and an energy transmission member 112 extending to the distal tip 106 and operatively coupling to the one or more treatment components. In the illustrated embodiment, the ablation treatment module 114 is capable of generating RF energy and passing the RF energy to the energy transmission member 112. The energy transmission member 112 is communicatively coupled to the elongated member to allow the RF energy to pass to the distal tip 106. In use, the distal tip 106 may be positioned at or near targeted tissue, and the transmitted RF energy heats the targeted tissue sufficiently to cause cell death. An actuator 113 (e.g., foot control) may be included to provide selective activation of the ablation treatment module 114.

As explained above, other embodiments may additionally or alternatively include other treatment modalities. For example, some embodiments may include one or more treatment components configured to provide cryotherapy, chemotherapy (e.g., alcohol), drug delivery, or combinations thereof. A treatment assembly may include a lumen extending through the elongated member to allow one or more agents to be delivered to the distal tip 106. Drug agents that may be delivered include, for example, cytotoxins, anti-fibrotic drugs, anti-inflammatory drugs, ion channel blockers and activators, and cytokines.

The illustrated system 100 also includes an electrical assembly comprising an electrical module 120, one or more electrical sensors disposed at the distal tip 106, and an electrically conductive member 116 extending to the distal tip 106 and operatively coupling to the one or more electrical sensors. In this particular embodiment, one or more electrodes at the distal tip 106 enable electrical readings of targeted tissue, as described in more detail below. The electrical assembly is configured to record electrical signals from targeted tissue. Electrical signals in cardiac tissue may be correlated to conduction pathways and/or regions of cellular dysfunction. Electrical signal measurements may include electric potentials (i.e., voltages), impedance, conductance, resistance, and the like. In the illustrated embodiment, electrical readings may be transmitted through the electrically conductive member 116. Other non-wired means of communication may additionally or alternatively be used, such as one or more signal senders (e.g., antennae and/or other transmission means) and corresponding receivers.

A sensor member 118 is also shown extending through the elongated member 102 toward the distal tip 106. The sensor member 118 is shown here as being coupled to the electrical module 120, but other sensor members may additionally or alternatively be coupled to other modules of the system 100. The sensor member may provide readings related to the environment of the distal tip 106, such as temperature, pressure, oxygen levels, pH, or other desired readings. In some embodiments, the sensor member is a thermistor, thermocouple, or other suitable temperature sensor known in the art.

The system 100 also includes a localization assembly comprising a localization module 140, a localization connecting member 142, and one or more localization components disposed at the distal tip 106. In this embodiment, the localization components are localization electrodes (described in more detail below). The localization assembly is configured to determine the location of the distal tip 106 within the three-dimensional working space. In some embodiments, the localization module 140 includes a reference electrode intended to remain in a fixed, reference position while the localization electrodes at the distal tip 106 are moved. The positional relationship between the reference electrode at the localization module 140 and the localization electrode(s) at the distal tip 106 thereby allows determination of the three-dimensional position of the distal tip 106. Other localization assembly embodiments may include, in addition to or as an alternative to electrode localization components, magnetic components, optical fiber components, and/or other components capable of providing localization of the distal tip 106.

Although the optical transmission member 108, energy transmission member 112, electrically conductive member 116, sensor member 118, and localization connecting member 142 are shown as passing into the handle 104 and through the elongated member 102 to the distal tip 106, it will be understood that they need not be configured as one integral piece, and one or more of the foregoing members may include multiple sections. For example, one section may connect to another section at a pin, plug, or other connector at the handle 104 and/or at other locations within the system 100. Further, the illustrated embodiment shows "wired" connections between the various modules 110, 114, 120, 122, 140 and the distal tip 106. However, in other embodiments, one or more of the modules 110, 114, 120, 122, and 140 may be operatively coupled to the distal tip 106 using a remote or "wireless" connection, such as via antennae or other wireless communication components. For example, in some embodiments the imaging assembly may comprise a camera at the distal tip 106, and the camera may be communicatively coupled to the imaging module 110 through a wired and/or wireless connection. In another example, voltages or other electrical signals may be relayed from the distal tip via one or more antennae to receivers located outside the patient's body.

The illustrated system 100 also includes a computer system 122 communicatively coupled to one or more of the imaging module 110, treatment module 114, electrical module 120, and localization module 140. Although the modules are shown here as physically separate units it will be understood that one or more of the illustrated modules may be combined and/or integrated with one another and/or with the computer system 122. Moreover, some embodiments may omit one or more of the illustrated modules, and not all embodiments necessarily include all of the illustrated components of the system 100. For example, some embodiments may omit the treatment assembly and/or electrical assembly.

Distal Tip Embodiments

Figure 2:
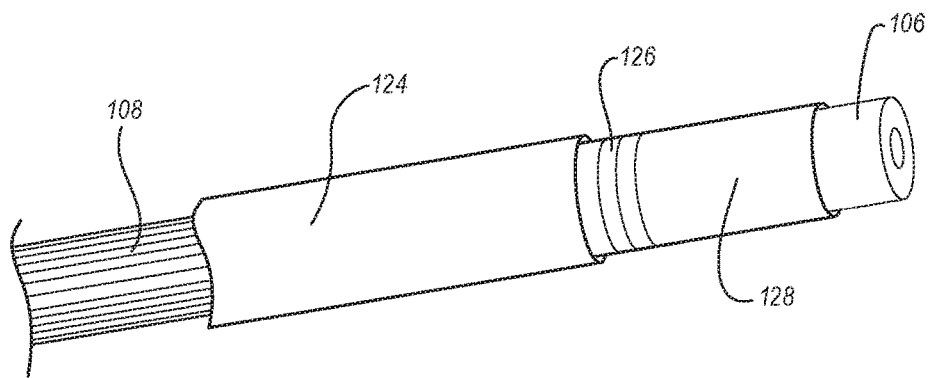
FIG. 2 illustrates a detailed view of a distal section of the elongated member shown in FIG. 1.

FIG. 2 illustrates a detailed view of the distal section of the elongated member 102 of FIG. 1. The outer sheath 124 is shown in partial cutaway view so that the inner optical transmission member 108 may be seen. Optical transmission member 108 is configured as a fiber optic bundle in this particular embodiment. A typical fiber optic bundle as used in the described embodiments is made up of 10,000 to 100,000 fibers, with an overall bundle diameter of about 1.2 to 2.4 mm, although alternative embodiments may utilize different fiber optic configurations based on particular application needs or preferences. For example, some embodiments may have an overall diameter of about 0.2 mm to 5 mm.

The illustrated device includes one or more localization electrodes 126 configured to provide relative position information within the three-dimensional working space. In presently preferred embodiments the localization electrodes 126 are configured as ring-shaped electrodes circumferentially positioned about the elongated member 102. Other embodiments may additionally or alternatively include different electrode shapes, such as linear (non-circular) shaped electrodes.

Figure 3:
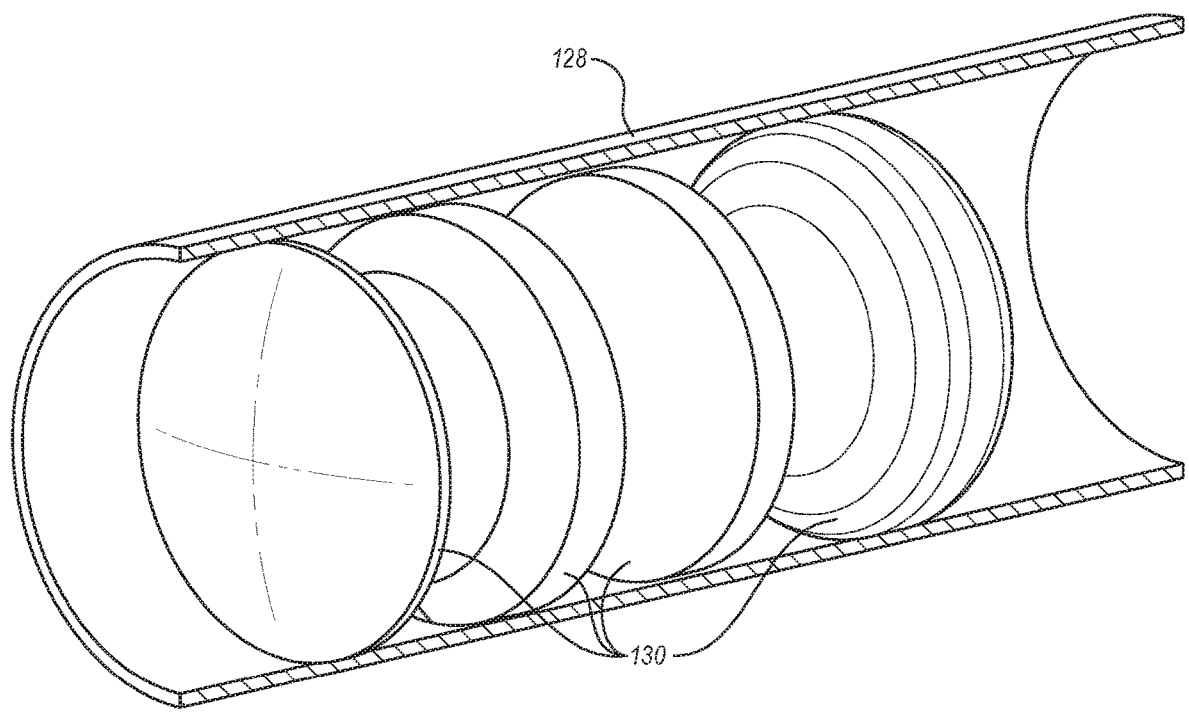
FIG. 3 illustrates an exemplary lens arrangement which may be included in the distal section of the device as part of an imaging assembly.

An optical housing 128 is also positioned near the distal tip 106. The optical housing 128 may include one or more imaging components that enable or augment operation of the imaging assembly. For example, as shown in FIG. 3, the illustrated optical housing 128 includes one or more lenses 130. The optical housing 128 may additionally or alternatively include other imaging components, such as an aperture, image sensor, light detector, other lens arrangements, and the like. Some embodiments may include an entire camera system within the optical housing 128 (e.g., may omit the optical transmission member 108). Such a camera system may be configured to communicate captured image data via antenna and/or proximally extending wire. However, presently preferred embodiments utilize an optical transmission member 108.

The illustrated lenses 130 allow light transferred through the optical transmission member 108 to be focused to a desired region or depth within targeted tissue. For example, the lenses 130 and other components of the imaging assembly may be configured to provide a depth of focus of at least about 5 µm, with common focal depths within a range of about 25 to 200 µm below the surface of targeted tissue (e.g., for typical fluorescence confocal imaging). Other imaging modalities such as multiphoton or hyperspectral imaging can allow imaging at greater depths. In implementations within the heart, the imaging assembly may be configured to visualize the subendocardial myocardium. As shown, the lenses 130 may be oriented with a common longitudinal axis parallel to the longitudinal axis of the optical housing 128.

The distal tip 106, optical housing 128, and localization electrode(s) 126 may be collectively referred to herein as a "tip structure." Alternative embodiments may position these components differently than as shown in FIG. 2. For example, some embodiments may position the optical housing 128 proximal of the localization electrode(s) 126, rather than distal of the localization electrode(s) 126. Some embodiments may omit the optical housing 128. For example, depending on the particular imaging modality utilized, some embodiments may not require lenses 130 and so may omit the optical housing 128.

Figure 4:
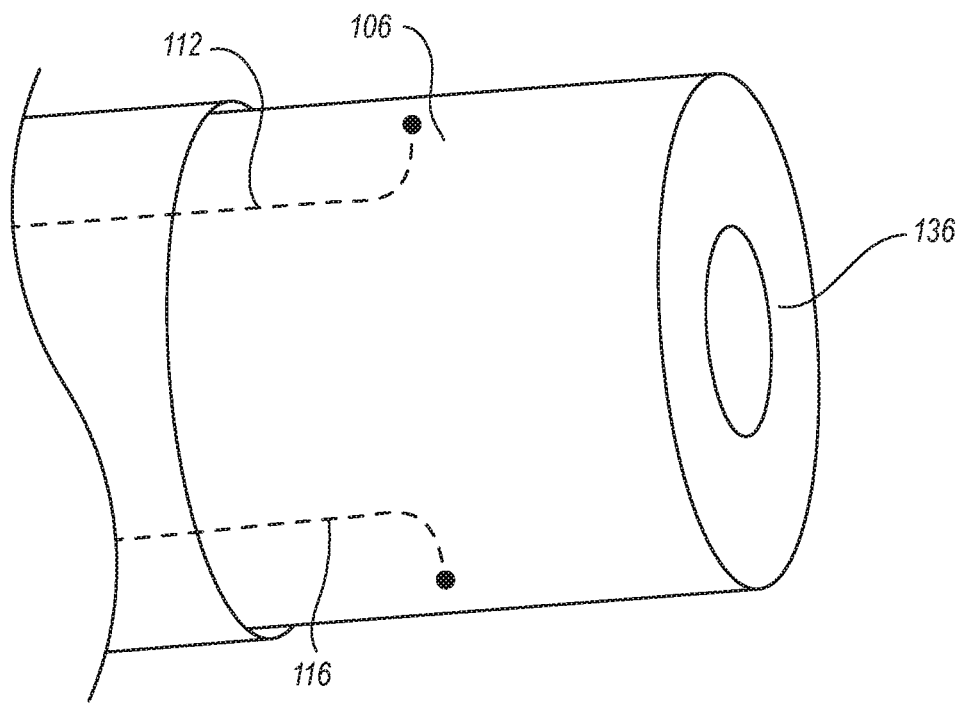
FIGS. 4 through 9 illustrate various distal tip configurations.

FIG. 4 illustrates a detailed view of the distal tip 106, showing an aperture 136 through which light can pass to allow imaging of nearby tissue. The distal tip 106 may be formed of any suitable, medical grade material. In embodiments that are configured to provide ablation and/or electrical signal reading, however, the distal tip 106 comprises or is formed of a metal or other suitably conductive material (e.g., gold, platinum, stainless steel, silver-silver-chloride, combinations thereof, etc.). As shown, the energy transmission member 112 or the electrically conductive member 116 may be operatively coupled to the distal tip 106 to provide, respectively, ablation functionality or electrical signal functionality. Where the distal tip 106 is formed as one integral piece, it is typically not possible for it to function, at the same time, as both an ablation electrode and an electrical signal measurement electrode without isolating each electrode dielectrically. Other distal tip embodiments described below with reference to FIGS. 5 through 9 include features allowing imaging and localization to be combined with treatment (e.g., ablation) and electrical mapping. Any of the following distal tip embodiments may be utilized with the other system components shown in FIGS. 1 through 3.

Figure 5:
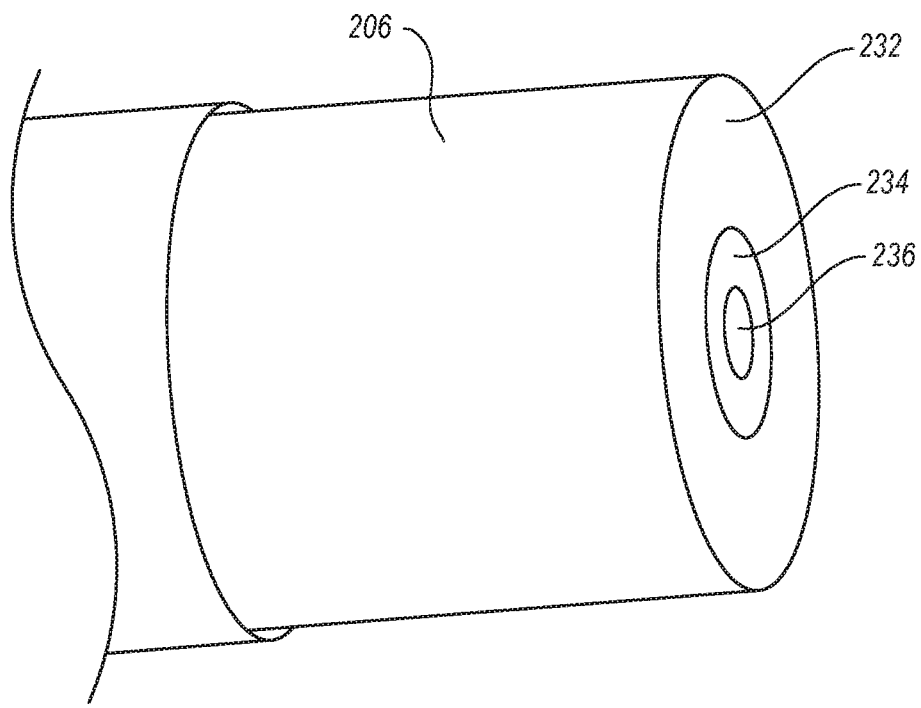

FIG. 5 illustrates a detailed view of a distal tip 206 having a first section 232 and a second section 234. The first section 232 and second section 234 may be suitably insulated from one another, formed of different materials, and/or otherwise configured to allow separate functions. For example, the first section 232 may be configured for ablation while the second section 234 is configured for reading electrical signals, or vice versa. As shown, the second section 234 is positioned circumferentially within the first section 232. The aperture 236 allows passage of light through the tip 206 to enable imaging.

Figure 6:
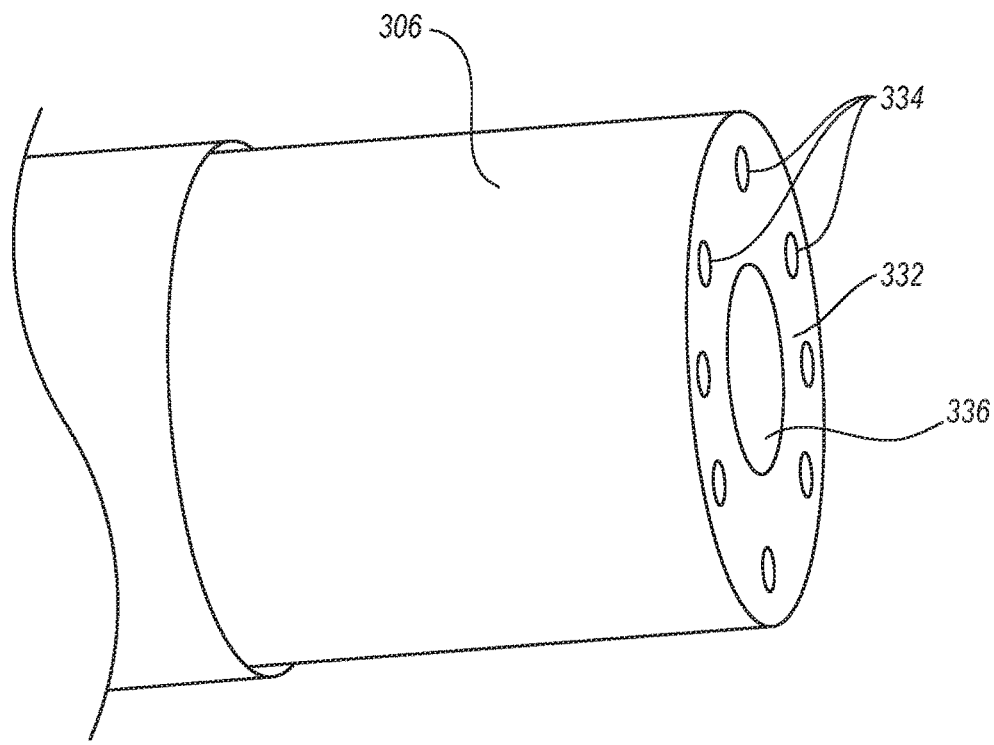

FIG. 6 illustrates a detailed view of a distal tip 306 having a first section 332 and a plurality of second sections 334 arranged circumferentially within the perimeter of the first section 332. As with the embodiment shown in FIG. 5, the first section 332 may function as a first type of electrode while the second sections 334 function as another type. For example, the first section 332 may be configured for ablation while the second sections 334 are configured for reading electrical signals, or vice versa. The aperture 336 allows passage of light through the tip 306 to enable imaging.

Figure 7:
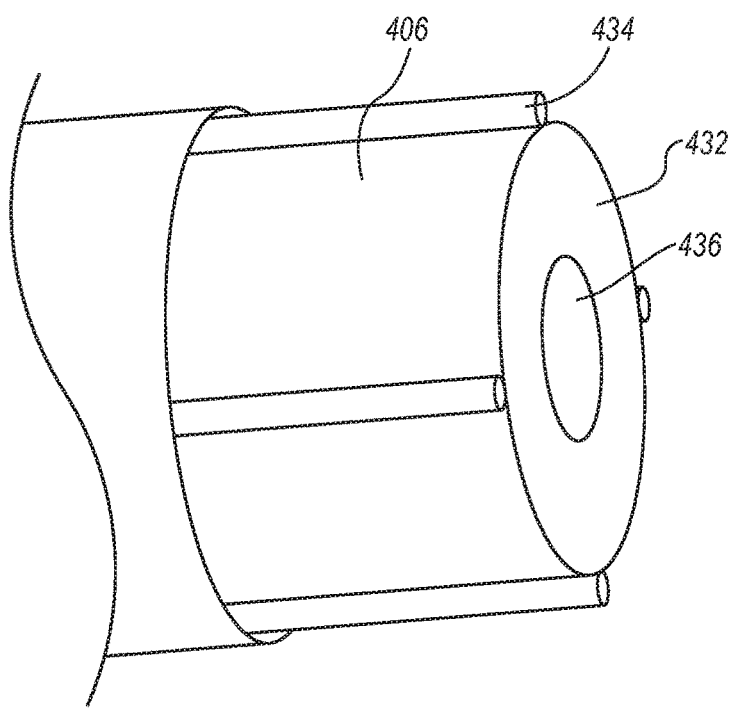

FIG. 7 illustrates a detailed view of a distal tip 406 having a first section 432 and a plurality of second sections 434 arranged outside the perimeter of the first section 432. As with the embodiments of FIGS. 5 and 6, the first section 432 and the second sections 434 may be configured to provide separate functionality. For example, the first section 432 may be configured for ablation while the second sections 434 are configured for reading electrical signals, or vice versa. The aperture 436 allows passage of light through the tip 406 to enable imaging.

Figure 8:
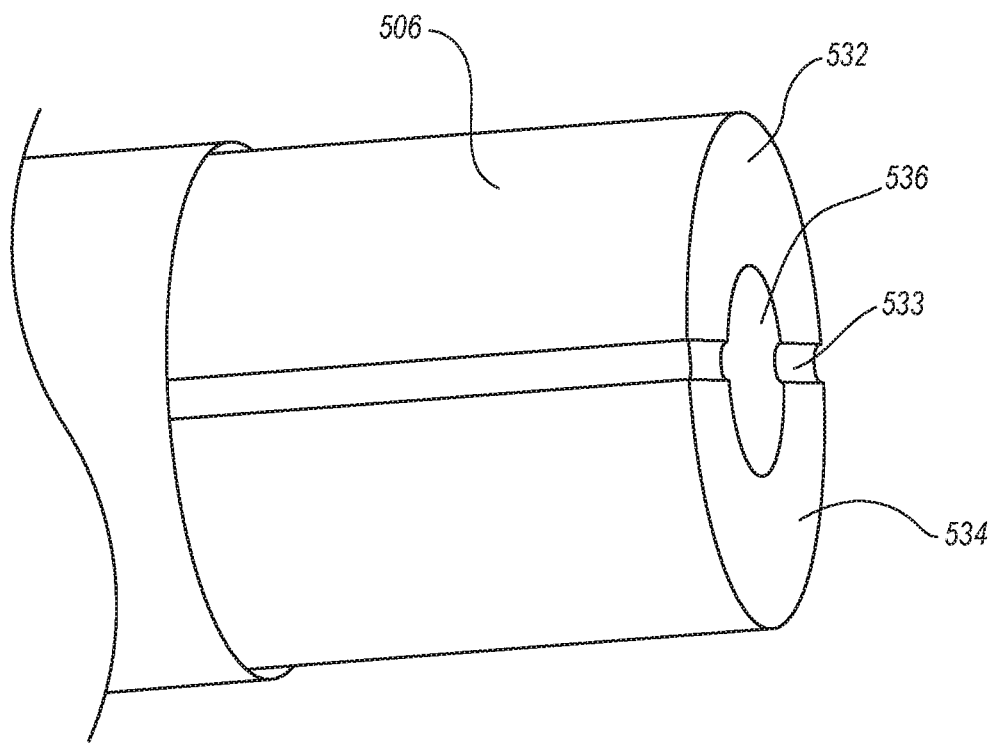

FIG. 8 illustrates a detailed view of a distal tip 506 having a first section 532 and a second section 534 separated by a border 533 extending substantially along the longitudinal axis. In some embodiments, the border 533 is formed of an electrically insulative material to suitable insulates the first section 532 from the second section 534. As with the embodiments of FIGS. 5 through 7, the first section 532 and second section 534 may have different functions. For example, one may be configured for ablation while the other is configured for reading electrical signals. The aperture 536 allows passage of light to enable imaging.

Figure 9:
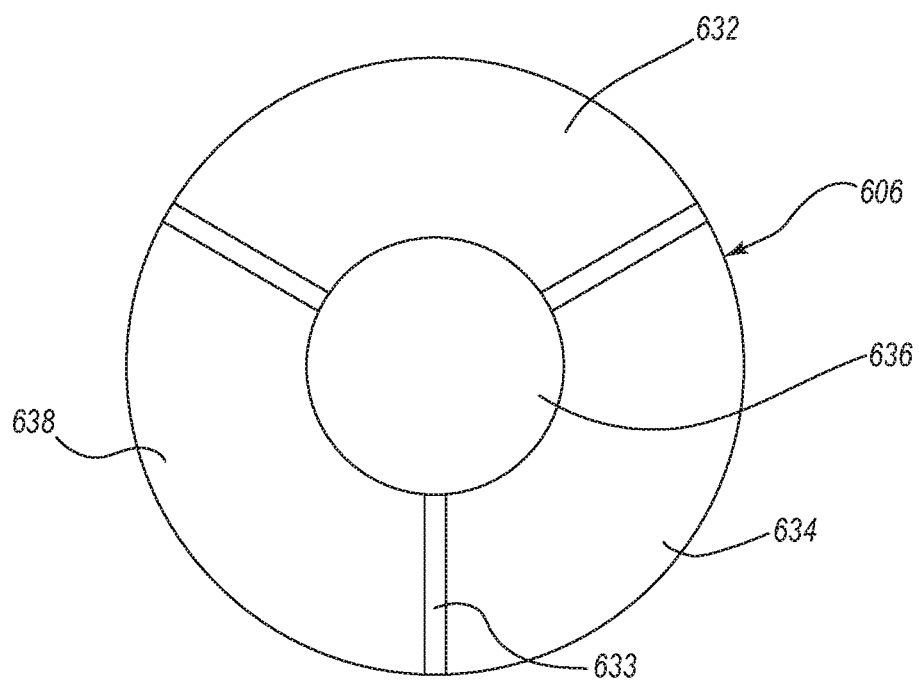

FIG. 9 illustrate a front view of an embodiment of a distal tip 606 similar to the embodiment of FIG. 8. Rather than two sections, the illustrated embodiment includes a first section 632, second section 634, and third section 638 separated by border 633. Each of the three sections may be configured to provide a different function. For example, one may be configured for ablation, another for reading electrical signals, and another for providing localization. As with other embodiments, the aperture 636 allows for the passage of light to enable imaging. Other embodiments may include more than three different types of distal tip sections to provide other distal tip functions as desired or according to particular application needs.

Transcatheter Approaches

Figure 10:
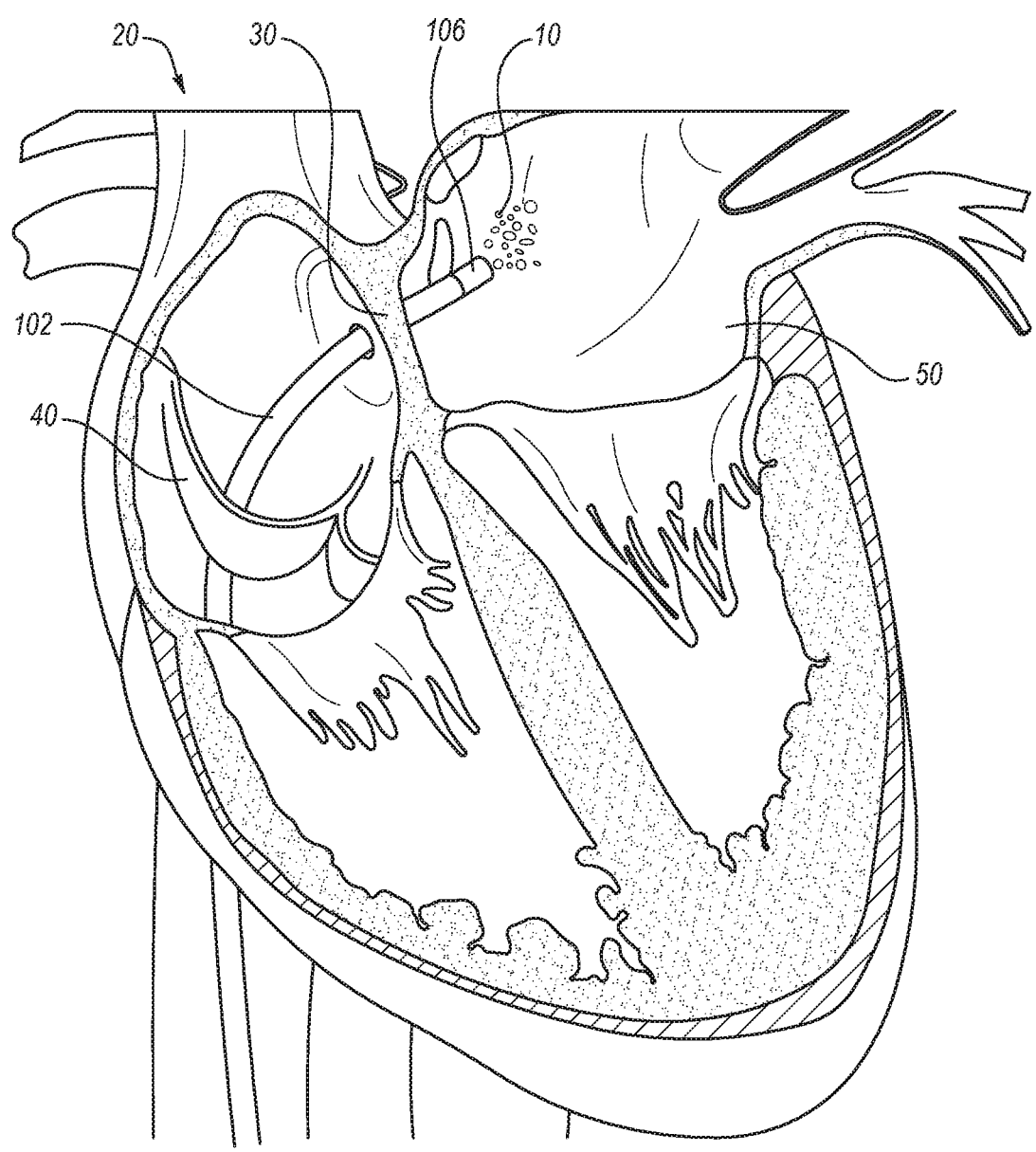
FIG. 10 illustrates an exemplary transcatheter approach for delivering a distal tip of the device to a targeted cardiac region.

FIG. 10 illustrates an exemplary transcatheter approach for delivering the distal tip 106 to targeted cardiac tissue, which is one exemplary method for delivering the distal tip of the elongated member to a targeted internal tissue in implementations where the targeted internal tissue is cardiac tissue. The illustrated example shows a transfemoral, transseptal approach for reaching the left atrium 50 of a heart 20. Other implementations may utilize other suitable transcatheter approaches and/or may target other areas of the heart. For example, the elongated member 102 may be inserted through a transapical, transradial, or transjugular approach, and/or the distal tip 106 may be directed to any of the other heart chambers or nearby cardiac tissues.

In the illustrated approach, the distal tip 106 is routed into the right atrium 40 through the inferior vena cava. The distal tip 106 is then passed through the septum 30 and into the left atrium 50, where it may be positioned at or near targeted tissue 10. The device 100 may beneficially be utilized in a blood-filled, beating heart in situ.

Once the distal tip 106 is positioned at or near targeted tissue 10, the device may be operated to obtain images of the myocardium, to measure electrical signals and/or other readings related to the anatomical environment (e.g., temperature, pH, etc.), to determine the three-dimensional location of the distal tip 106, and/or to treat (e.g., ablate) the targeted tissue 10. The distal tip 106 may then be moved to another location within the heart to image, treat, measure electrical signals and/or other environmental readings, and/or determine location. This may be repeated until the device has been operated at a desired number of locations. A resulting fibrosis and/or electrical map will have greater resolution and/or extent as the number of measured locations goes up. Measurements/images taken at a range of about 50 to 100 different locations will typically be sufficient, though less or more may be used depending on particular application needs.

Figure 11A:
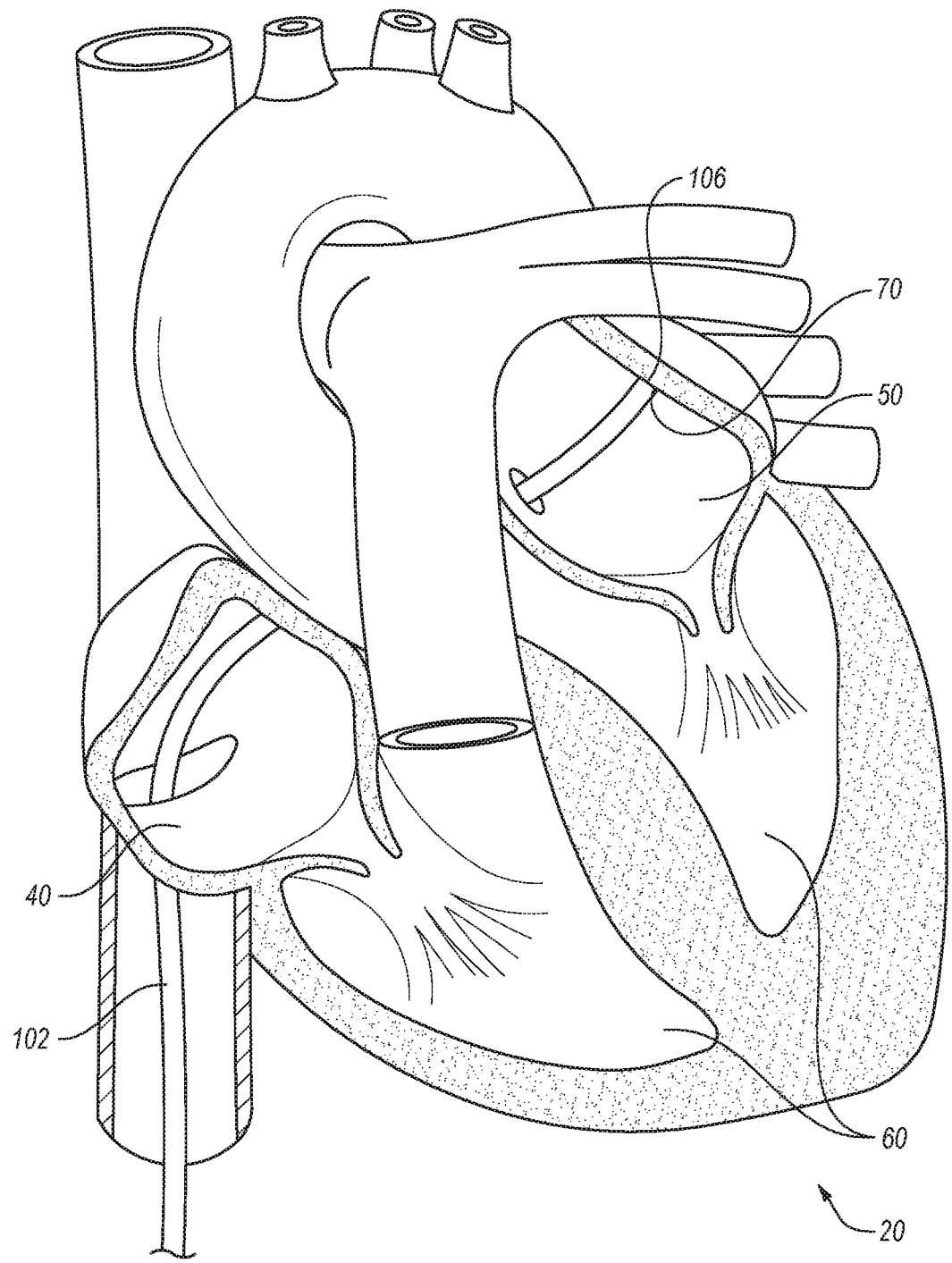
FIGS. 11A through 11C illustrate anchoring of the distal tip of the device against a targeted contact point to beneficially enable operation in a blood-filled, beating heart without necessarily relying on triggering of imaging or readings based on the cardiac cycle.
Figure 11B:
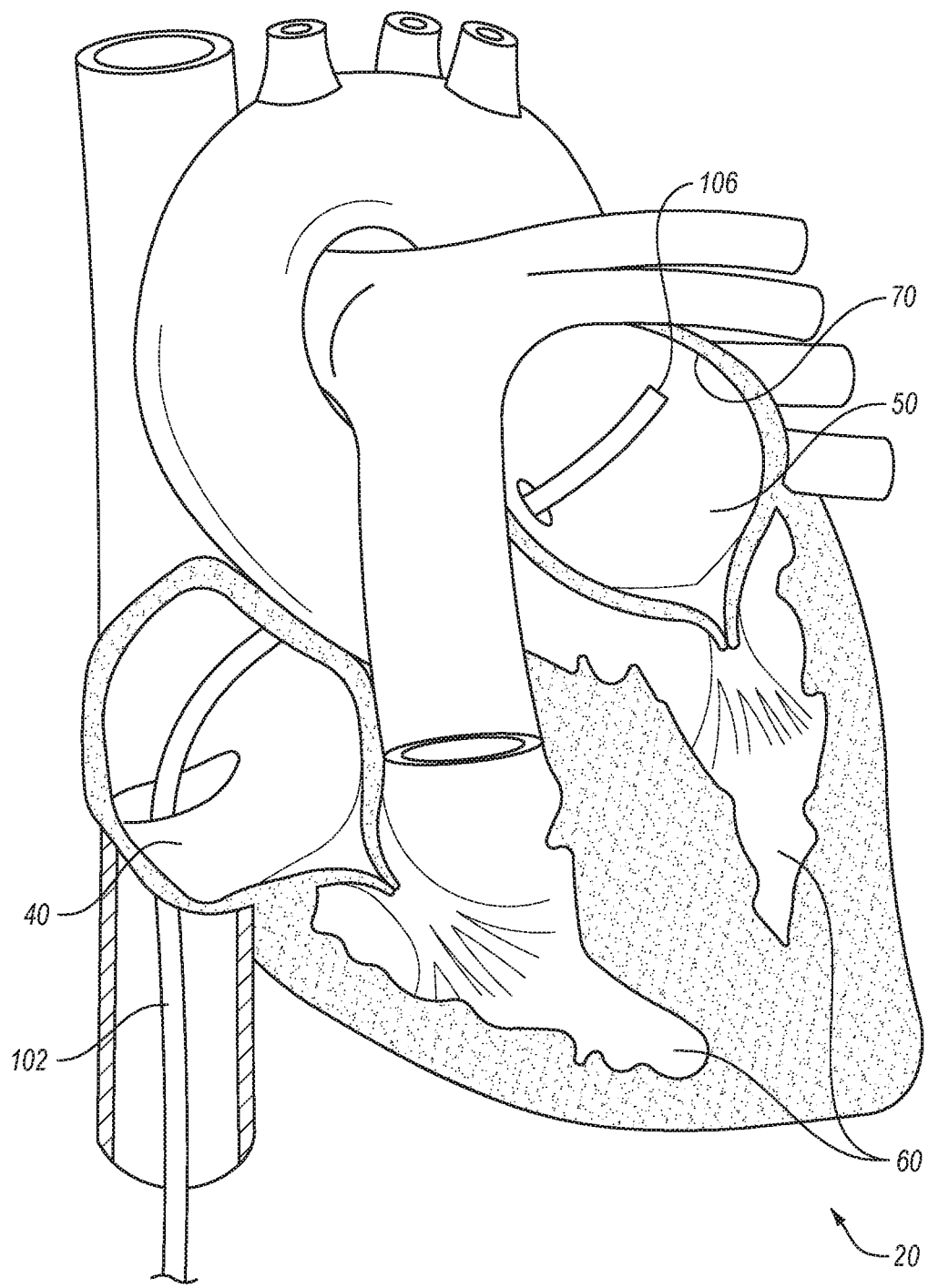
Figure 11C:
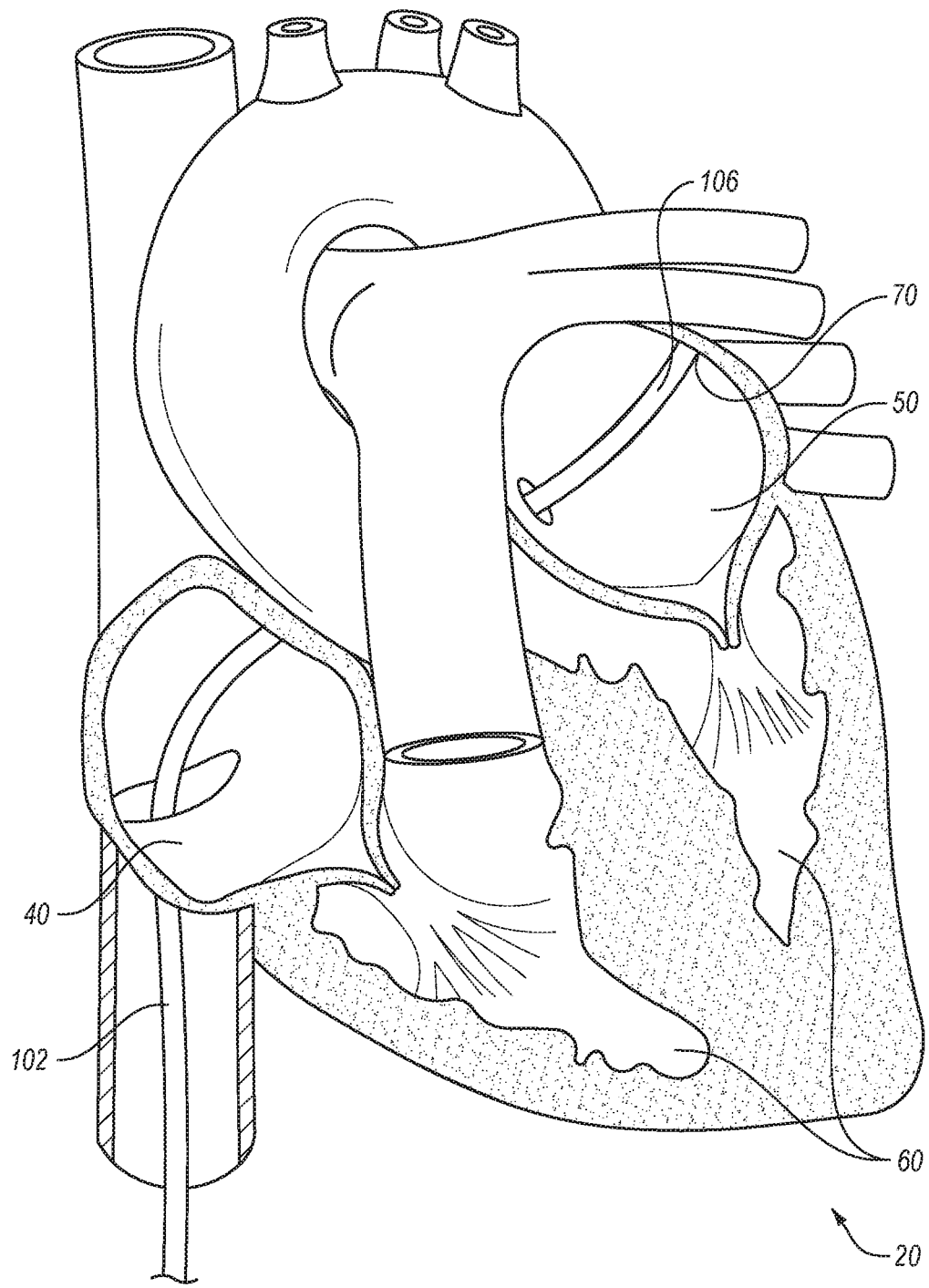

FIGS. 11A-11C illustrate a beneficial feature of the elongated member 102 that provides effective contact with the targeted tissue. FIG. 11A shows the distal tip 106 of the elongated member 102 positioned against a contact point 70 in the left atrium 50. The heart 20 is in ventricular diastole, where the atria 40, 50 are contracted and the ventricles 60 are dilated. FIGS. 11B and 11C show the heart 20 in ventricular systole, where the atria 40, 50 are dilated and the ventricles 60 are contracted. As the beating heart moves between ventricular diastole and ventricular systole, it can become difficult to maintain the distal tip 106 in an appropriate position relative to the intended contact point 70. For example, the distal tip 106 is shown in contact with contact point 70 in FIG. 11A, but the contact point 70 is shown as expanding away from the distal tip 106 in FIG. 11B as the heart 20 transitions to ventricular systole.

Advantageously, it was found that when the distal section (i.e., the portion extending at least 2 cm from the distal end) of the elongated member 102 is configured with the appropriate flexibility profile, and when gentle distally-oriented axial force and/or manual deflection (e.g., using control handle 104) is applied to the elongated member 102, the distal tip 106 was able to maintain contact with the contact point 70 throughout the cardiac cycle. Thus, rather than losing contact with the contact point 70 during tissue motion, as shown in FIG. 11B, the distal tip 106 is able to maintain contact with the contact point 70, as shown in FIG. 11C. For a typical embodiment where the distal section of the elongated member has a diameter (not including the sheath) of about 1.2 to 1.4 mm, and a stiffness of about 2 to 6 N/m (or more preferably about 2.5 to 5 N/m or about 3.0 to 4.5 N/m), the axial force needed to provide this benefit is greater than about 0.13 gram-force, but not so great as to cause any trauma to the contacted tissue.

Methods of Generating a Tissue Map

Figure 12:
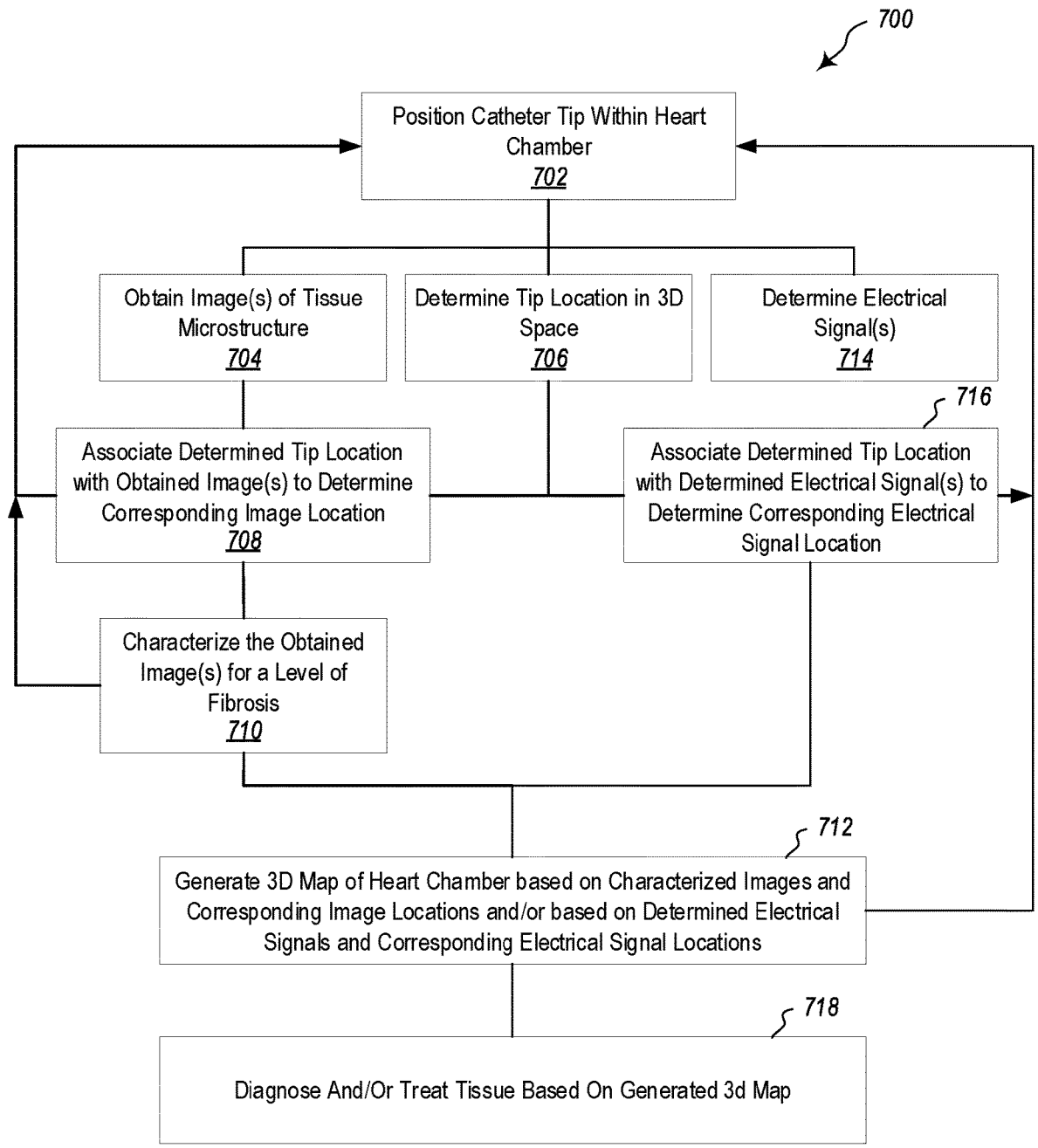
FIG. 12 illustrates an exemplary method for generating a three-dimensional tissue map.

FIG. 12 illustrates an exemplary method 700 for generating a tissue map. In the particular example shown in FIG. 12, the tissue map is a three-dimensional map of a targeted heart chamber. Any of the system/device embodiments described above in relation to FIGS. 1 through 11C, or combinations thereof, may be utilized to perform method 700.

The method 700 includes a step 702 of positioning a catheter tip within a heart chamber. Once the catheter tip has been positioned at a first tissue location, the device may be used to obtain one or more images of tissue microstructure at the first location (step 704), and to determine the location of the distal tip in the three-dimensional working space (step 706).

The illustrated method 700 further includes a step of associating the determined location (from step 706) with the one or more images obtained at the first tissue location, thereby providing a determined image location (step 708). The steps of positioning the catheter tip (step 702) and obtaining one or more images of tissue microstructure (step 704), determining the location of the tip in three-dimensional space (706), and associating the determined location with the obtained image(s) (step 708) may then be repeated to obtain additional images at different determined tissue locations.

The method 700 further includes a step of characterizing the obtained tissue microstructure images according to a level of fibrosis (step 710). This step may be performed intermittently throughout the imaging process (e.g., after each image is obtained and/or after each image location is determined) or in batch (e.g., after several or even all of the images are obtained). Other embodiments may additionally or alternatively characterize the obtained images according to one or more other tissue microstructure attributes. For example, images may be characterized according to cell size, cell regularity, tissue regularity, dye uptake (e.g., as shown by exhibited fluorescence/brightness), other tissue microstructure attributes, and combinations thereof.

The fibrosis characterization may be accomplished using one or more computer-implemented image processing techniques. In some embodiments, the level of fibrosis shown by an image is determined by measuring the average pixel intensity for a predetermined area or field of view. In FCM, fibrotic cardiac tissue will appear brighter relative to normal, healthy cardiac tissue. Thus, a higher area fraction of bright regions in an image corresponds to higher levels of fibrosis. Additionally, or alternatively, the level of fibrosis in an image may be determined by measuring the spatial regularity of the image. Healthy myocardium exhibits a regular striated arrangement of muscle cells and capillaries, whereas fibrotic, injured, or ablated myocardium will have less striations and regularity. This is believed to occur because fluorescent dye utilized during the imaging process more readily diffuses into fibrotic tissues and damaged cells, which more uniformly distributes the fluorescent signal. This process is explained in more detail in the Examples section below.

The method 700 also optionally includes the parallel steps of, at each selected tissue location, determining one or more electrical signals (step 714) and associating the determined tip location with the one or more electrical signals to determine a corresponding electrical signal location (step 716). This may include, for example, mapping voltages along multiple tissue locations in the heart chamber.

The method 700 also includes a step of generating a three-dimensional map of the heart chamber based on the characterized images and corresponding image locations and/or based on the determined electrical signals and corresponding electrical signal locations (step 712). Various rendering schemes may be used to render the three-dimensional map. The method 700 may also include a step of diagnosing and/or treating targeted tissue within the heart chamber based on the generated map (step 718). For example, candidate tissue may be ablated or otherwise treated in-situ and in real time based on the obtained imagery and/or electrical signal data. In some embodiments, tissue may be imaged and/or electrically measured following treatment to assess the effects of the treatment.

Tissue Map Rendering

Figure 13A:
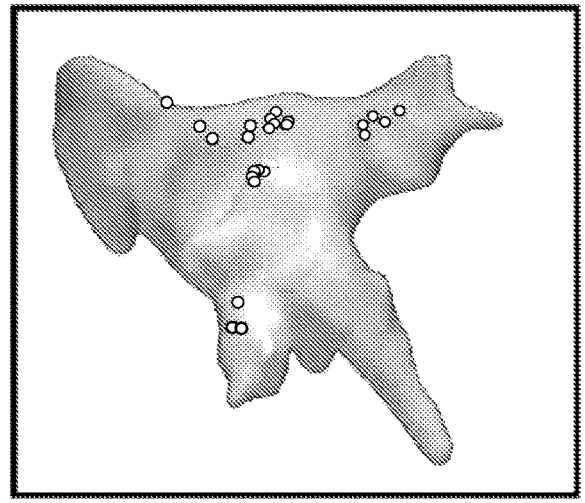
FIGS. 13A and 13B illustrate an exemplary rendering of a three-dimensional fibrosis map.
Figure 13B:
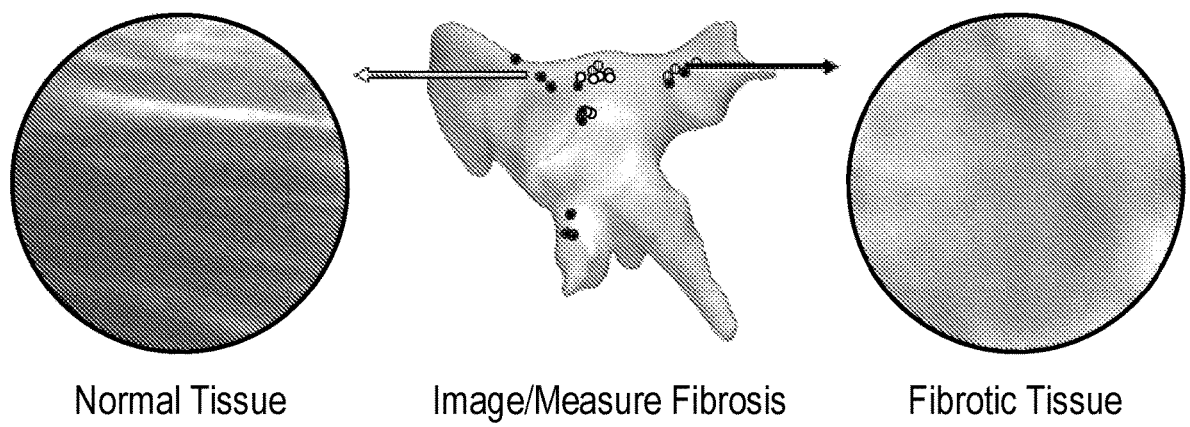

FIGS. 13A and 13B illustrate an example of a three-dimensional fibrosis map. As shown in FIG. 13A, imaged locations are rendered as different points within the three-dimensional space. As shown in FIG. 13B, the obtained tissue microstructure images corresponding to the determined locations are characterized according to a level of fibrosis. In this particular example, images are discretely characterized as "Normal Tissue" (shown as white points), "Fibrotic Tissue" (shown as black points) or medium/intermediate tissue (shown as hatched points). The imaged locations are rendered on the three-dimensional map accordingly so that each point represents a point of normal tissue, fibrotic tissue, or intermediate tissue.

Of course, alternative embodiments may characterize the imaged locations using a simple binary characterizing scheme, by characterizing using a granularity greater than three categories, or by characterizing in a non-discrete manner, such as by assigning each image a fibrosis "score" along a spectrum. Differential rendering may be based on color differences, texture differences, shading differences, brightness differences, glyphs, or other suitable differential rendering techniques.

FIGS. 14A and 14B illustrate an alternative rendering scheme where regions between imaged locations are rendered by interpolating between imaged locations. The discrete point rendering shown in FIG. 14A may be converted to the "heat-map" style rendering shown in FIG. 14B using a suitable interpolation algorithm. Other suitable data rendering schemes known in the art may also be utilized to render the three-dimensional map.

Figure 16A:
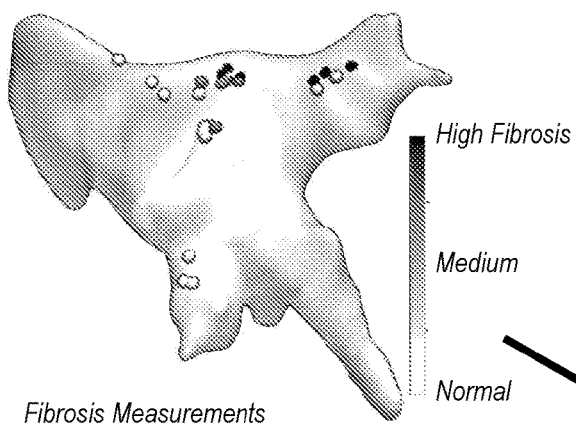
Figure 16B:
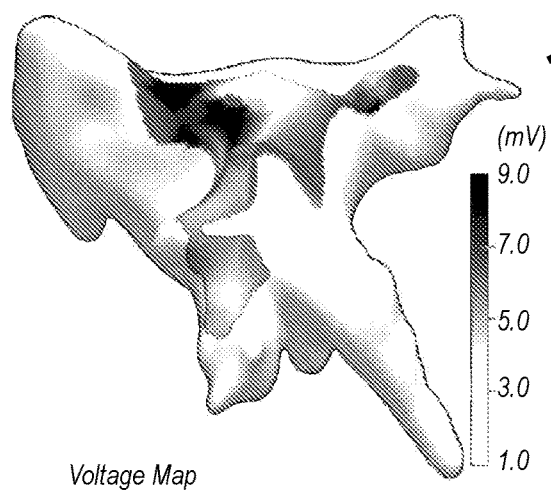
Figure 16C:
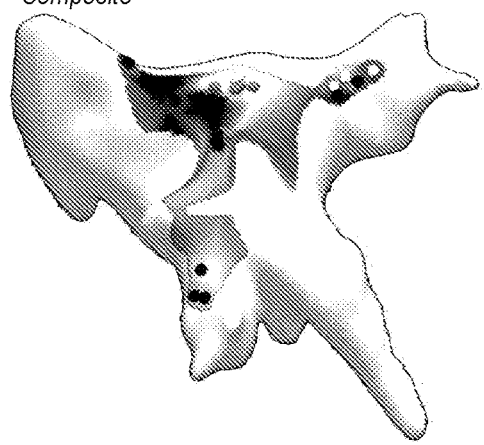

FIGS. 15A through 15C illustrate creation of an exemplary composite map (shown in FIG. 15C) by combining mapped voltage measurement points (shown in FIG. 15A) with a fibrosis map (shown in FIG. 15B). In this example, the fibrosis map is rendered as a heat-map while the voltage measurements are overlaid as points on the map where point color difference reflect different voltage measurements. FIGS. 16A through 16C similarly illustrate creation of a composite map (shown in FIG. 16C) by combining fibrosis measurement points (shown in FIG. 16A) with a voltage map (shown in FIG. 16B). In this example, the voltage map is rendered as a heat-map while the fibrosis measurements are overlaid as points on the map. Other composite maps may utilize different overlay and/or rendering schemes known in the art, such as by using different transparency levels, different color schemes, and/or different highlighting effects for each of the different data types.

EXAMPLES

We performed real-time FCM during focal RF ablation using an integrated imaging/ablation catheter. The integrated catheter was positioned on the endocardial surface of various regions within the left atrium of the beating heart in canine. Following intravenous injection of fluorescein sodium, we acquired continuous image sequences of the subendocardial myocardium as RF energy was applied for 8 s at a maximum power of 30 W to produce a tissue temperature 60-80° C.

Figure 17A:
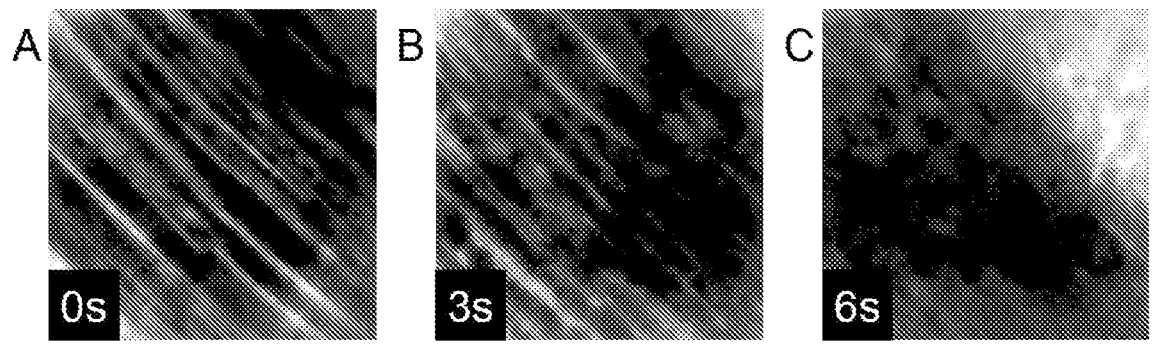
FIGS. 17A through 17C illustrate images and related data from an exemplary real-time FCM process with focal RF ablation using an integrated imaging/ablation catheter.

Representative results from the left atrial subendocardial myocardium obtained during ablation using the integrated catheter are shown in FIG. 17A. Prior to ablation, the regular striated arrangement of working myocardium was apparent within the images (0 s, Panel A). In addition, myocyte shortening in the image region was visible. In contrast, the characteristic striations and cell shortening gradually diminished during the ablation (Panels B and C at 3 and 6 s, respectively).

We explain the decrease in striations by fluorescent dye diffusing from the interstitial space into the cell interior as a result of heat-induced perforation of cellular membranes. The result of membrane damage is cell death. Our data suggest that we can identify cell death as transition of the fluorescent signal from striated to a more uniform distribution.

Figure 17B:
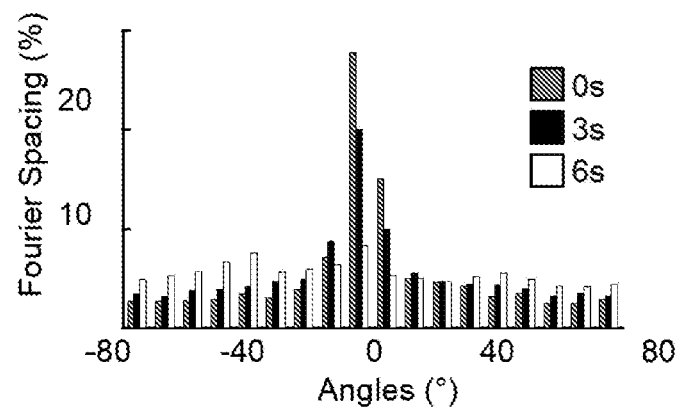
Figure 17C:
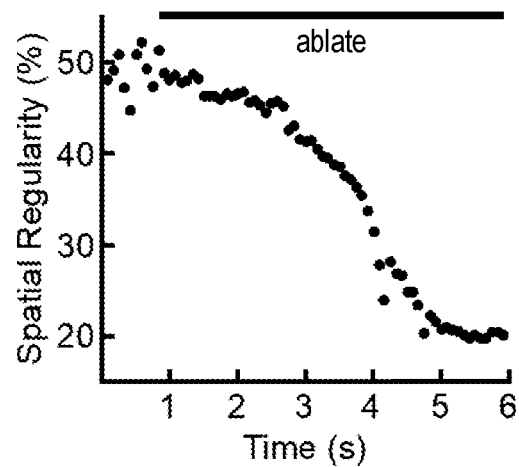

Image processing techniques were used to quantitatively characterize cell and tissue damage from these image sequences. FIG. 17B presents the ratioed intensity distribution vs. orientation angles from Fourier analysis of the images in FIG. 17A. The image acquired prior to ablation (0 s, Panel A of FIG. 17A) exhibited a more pronounced peak in its intensity distribution as compared to those images acquired during the ablation (Panels B and C of FIG. 17A at 3 and 6 s, respectively), indicating more uniform distribution. We quantified the peakness as a measure of spatial regularity of striations for all images of the sequence (FIG. 17C, with horizontal "ablate" bar representing the ablation window). We observed a decay in the spatial regularity that was associated with the ablation.

As shown, a spatial regularity of at least about 40% or at least about 50% generally correlated with healthy tissue, while a spatial regularity of below about 30% or below about 20% correlated with dying/damaged tissue. Other threshold levels (e.g., other histogram-derived thresholds) may be used as appropriate given different particular tissue features and/or application requirements.

What is claimed is:

1. An intravascular device configured for in-situ imaging, at a microstructure level, of tissue within a patient's body, the device comprising:
   an elongated member having a proximal end and a distal end;
   a distal tip disposed at or near a distal end of the elongated member and being configured for delivery to a targeted tissue within a patient's body;
   an imaging assembly configured to provide forward-facing microstructure imaging at a depth within targeted tissue, the imaging assembly including an optical transmission member extending within the elongated member and a forward-facing aperture disposed at the distal end of the elongated member, wherein the forward-facing aperture is substantially centered with respect to a longitudinal axis of the elongated member, and wherein the optical transmission member is axially aligned with the forward-facing aperture;
   a localization assembly configured to provide location information of the distal tip within a three-dimensional anatomical working space, the localization assembly including one or more localization electrodes disposed at or near the distal tip; and
   an electrical assembly comprising one or more electrical sensors disposed at or near the distal tip, the electrical sensors configured to contact targeted tissue and measure one or more electrical signals at the targeted tissue when the distal tip is contacted against the targeted tissue.

2. The device of claim 1, wherein the one or more localization electrodes are configured to provide positional data relative to a reference electrode.

3. The device of claim 1, further comprising a treatment assembly having one or more treatment components disposed at the distal tip for treating targeted tissue.

4. The device of claim 3, wherein the treatment assembly includes an energy transmission member which extends through the elongated member and is operatively coupled to the distal tip, the energy transmission member being capable of transmitting energy to the distal tip to enable ablation of targeted tissue at or near the distal tip.

5. The device of claim 4, wherein the energy transmission member is configured to transmit RF energy to the distal tip, and wherein at least a portion of the distal tip is configured as an ablation electrode conductive to RF energy to enable the RF energy to pass through the distal tip and toward a targeted tissue.

6. The device of claim 4, further comprising a temperature sensor operatively joined to the distal tip to enable temperature measurement at the distal tip.

7. The device of claim 3, wherein the treatment assembly is configured for delivering one or more of a treatment chemical, cryotherapeutic agent, or drug.

8. The device of claim 1, wherein the imaging assembly is configured to provide imaging of the targeted tissue at a depth of about at least 5 um.

9. The device of claim 1, wherein the imaging assembly is configured to provide images at a sub cellular and/or submicron resolution.

10. The device of claim 1, wherein the one or more electrical sensors are operatively coupled to an electrically conductive member to enable the distal tip to measure electrical signals, the electrically conductive member extending through the elongated member to the distal tip.

11. The device of claim 1, further comprising:
a treatment assembly operatively coupled to a first section of the distal tip
wherein the electrical assembly is operatively coupled to a second section of the distal tip,
wherein the first section of the distal tip is configured as an ablation electrode capable of conducting energy to targeted tissue, and
wherein the second section of the distal tip is configured as an electrical electrode capable of measuring voltages at targeted tissue.

12. A system configured for generating a three-dimensional map of tissue microstructure, the system comprising:
the intravascular device of claim 1; and
a computer system having one or more processors and one or more hardware storage devices having stored thereon computer-executable instructions which are executable by the one or more processors to cause the computer system to—
receive a plurality of forward-facing tissue microstructure images obtained by the intravascular device;
determine a location within the three-dimensional anatomical working space for each of the tissue microstructure images to obtain a plurality of image locations;
characterize each of the forward-facing tissue microstructure images according to an exhibited level of a tissue microstructure attribute; and
based on the characterized images, and based on the corresponding image locations, generate a three-dimensional tissue microstructure attribute map of the anatomical working space.

13. The system of claim 12, wherein each tissue microstructure image is characterized according to an exhibited level of a tissue microstructure attribute by determining one or more of image spatial regularity, average pixel intensity, and area fraction of bright regions, where bright regions are determined according to a brightness threshold.

14. The system of claim 12, wherein the computer system further comprises a user interface device, and wherein the computer-executable instructions are further configured to cause the computer system to render the three-dimensional attribute map on the user interface device.

15. The system of claim 12, wherein the electrical assembly enables the distal tip to measure electrical readings at targeted tissue, and wherein the computer-executable instructions are further configured to cause the computer system to:
receive a plurality of tissue electrical readings obtained by the intravascular device;
determine a location within the three-dimensional anatomical working space for each of the tissue electrical readings to obtain a plurality of electrical reading locations; and
based on the electrical readings and their corresponding locations, generate a three-dimensional electrical map of the anatomical working space associating the plurality of tissue electrical readings with their corresponding locations within the anatomical working space.

16. The system of claim 15, wherein the computer-executable instructions are further configured to cause the computer system to combine the tissue microstructure attribute map and the electrical map into a composite map.

17. The system of claim 16, wherein the computer system further comprises a user interface device, and wherein the computer-executable instructions are further configured to cause the computer system to render the composite map on the user interface device.

18. A method for generating a three-dimensional fibrosis map of a heart or portion thereof, the method comprising:
providing the intravascular device
of claim 1;
directing the distal tip of the intravascular device to a plurality of locations within the heart;
at each location, operating the intravascular device to obtain one or more forward-facing tissue microstructure images;
at each location, operating the intravascular device to determine the location of the distal tip within the three-dimensional anatomical working space;
associating each forward-facing tissue microstructure image with its corresponding determined location within the anatomical working space;
at each location, operating the intravascular device to obtain one or more electrical readings while the distal tip is in contact with cardiac tissue;
characterizing each forward-facing tissue microstructure image according to a level of exhibited fibrosis; and
based on the characterized images and their corresponding locations, generating a three-dimensional fibrosis map of the anatomical working space.

19. The method of claim 18, wherein the heart is a blood-filled, beating heart in situ.

20. The method of claim 18, wherein the intravascular device further comprises one or more electrical sensors disposed at the distal tip, the method further comprising:
at each location, operating the intravascular device to obtain one or more electrical readings;
associating each electrical reading with its corresponding determined location within the anatomical working space based on the obtained electrical readings and their corresponding locations, generating a three-dimensional electrical map of the anatomical working space; and
combining the electrical map and the fibrosis map to generate a composite map.

21. The device of claim 1, further comprising one or more lenses axially aligned with the forward-facing aperture.

\* \* \* \* \*